US010046039B2

(12) United States Patent
Ella et al.

(10) Patent No.: US 10,046,039 B2
(45) Date of Patent: Aug. 14, 2018

(54) BACTERIAL VACCINE AND METHODS FOR MANUFACTURE THEREOF

(71) Applicant: Bharat Biotech International Limited, Hyderabad (IN)

(72) Inventors: Krishna Murthy Ella, Hyderabad (IN); Venkatesan Ramasamy, Hyderabad (IN); Mandalapu Gangadhara Naidu, Hyderabad (IN)

(73) Assignee: Bharat Biotech International Limited, Hyderabad (IN)

( * ) Notice: Subject to any disclaimer, the term of this patent is extended or adjusted under 35 U.S.C. 154(b) by 43 days.

(21) Appl. No.: 14/913,816

(22) PCT Filed: Aug. 19, 2014

(86) PCT No.: PCT/IN2014/000530
§ 371 (c)(1),
(2) Date: Feb. 23, 2016

(87) PCT Pub. No.: WO2015/029056
PCT Pub. Date: Mar. 5, 2015

(65) Prior Publication Data
US 2016/0206721 A1 Jul. 21, 2016

(30) Foreign Application Priority Data

Aug. 24, 2013 (IN) ............................ 3750/CHE/2013

(51) Int. Cl.
*A61K 39/112* (2006.01)
*C12N 1/20* (2006.01)
*A61K 39/165* (2006.01)
*A61K 39/385* (2006.01)
*C12N 7/00* (2006.01)
*A61K 39/00* (2006.01)

(52) U.S. Cl.
CPC ........ *A61K 39/0275* (2013.01); *A61K 39/165* (2013.01); *A61K 39/385* (2013.01); *C12N 7/00* (2013.01); *A61K 2039/545* (2013.01); *A61K 2039/55* (2013.01); *A61K 2039/6037* (2013.01); *A61K 2039/70* (2013.01); *C12N 2760/18434* (2013.01); *Y02A 50/482* (2018.01); *Y02A 50/484* (2018.01)

(58) Field of Classification Search
None
See application file for complete search history.

(56) References Cited

U.S. PATENT DOCUMENTS 6,797,275 B1 9/2004 Kossaczka

FOREIGN PATENT DOCUMENTS

| CA | 2674345 | 10/2008 |
|---|---|---|
| CN | 1404873 | 2/1997 |
| IN | 2687/DEL/2005 | 2/2009 |
| WO | WO1095/DELNP/2006 | 1/2011 |
| WO | WO 2013/038375 | 3/2013 |
| WO | WO 2013/114268 | 8/2013 |
| WO | WO/2014009971 | 1/2014 |

OTHER PUBLICATIONS

Rodini et al (Clinical and Vaccine Immunology (2011), 18(3), 460-468).*
Hyun, J., et al., "Optimization of Vi capsular polysaccharide production during growth of *Salmonella enterica* serotype Typhi Ty2 in a bioreactor," *J. of Biotechnology* 135:71-77 (2008).
Szu et al. *Relation between Structure and Immunologic Properties of the Vi Capsular Polysccharide'* Infection and Immunity, Dec. 1991, p. 455-4561.
Search Report for EP Application No. 14841291.9 dated Nov. 24, 2017.
Sushant Sahastrabuddhe, International Vaccine Institute IAP COI Meeting Aug. 2012.
F. Micoli et al., Vi-CRM197 as a new conjugate vaccine against *Salmonelle typhi*; Vaccine 29:712-720 (2011).
J.F.G. Vliegenthart, Carbohydrate based vaccines; FEBS Letters:2945-2950 (2006).
Vadrevu Krishna Mohan et al., Safety and Immunogenicity of a Vi Polysaccharide-Tetanus Toxoid Conjugate Vaccine (Typbar TVC) in Healthy Infants, Children, and Adults in Typhoid Endemic Areas; Clinical Infectous Disease 61(3):393-402 (2015) published Apr. 13, 2015.
Wei Zhou, Preparation of Glycoconjugate Vaccines; Carbohydrate=Based Vaccines and Immunotherapies; ISBN 978-0-470-19756-1; Jan. 1, 2009.

* cited by examiner

*Primary Examiner* — Jennifer E Graser
(74) *Attorney, Agent, or Firm* — Remenick PLLC

(57) ABSTRACT

Disclosed are stable conjugate vaccine formulations for protection against *Salmonella typhi*, and methods of conjugation between Vi-polysaccharide of *S. typhi* to tetanus toxoid as the carrier protein, responsible for producing improved T-dependent immune response against Typhoid fever caused by *Salmonella typhi*. The methods disclosed in this invention and the resulting formulations are capable of inducing immunity against typhoid fever including in children below 2 years of age, through only a single injection to comprise a complete vaccination schedule.

11 Claims, 12 Drawing Sheets

BACTERIAL VACCINE AND METHODS FOR MANUFACTURE THEREOF

CROSS REFERENCE TO RELATED APPLICATIONS

This application is a national phase application under 35 U.S.C. § 371 of International Application No. PCT/IN2014/000530, filed on Aug. 19, 2014, which claims priority to Indian Patent Application No. 3750/CHE/2013, filed on Aug. 24, 2013; the disclosures of which are incorporated by reference herein.

FIELD OF THE INVENTION

The invention relates to the field of bacterial vaccine characterized to raise adequate immune responses in infants, children and adults against typhoid fever. Particularly, the present invention relates to conjugate vaccines and processes of manufacture thereof, wherein the native polysaccharides of *Salmonella typhi* are conjugated to carrier proteins and formulated as a prophylactic conjugate vaccine. Furthermore, this invention also relates to the field of combined vaccine formulations for protection against *Salmonella typhi* and measles virus.

BACKGROUND OF THE INVENTION

*Salmonella typhi*, the causative bacterium for typhoid fever in human beings is a major endemic disease in Africa, Asia, and Middle East. Food and water contaminated with *S. typhi* bacterium was identified as major source in transmission of the disease. Various studies have shown that the global burden of typhoid fever varies in different parts of the world. More than 100 cases in 100,000 populations per year reported in South Central Asia and South-East Asia; Asia, Africa, Latin America and the Caribbean are estimated to have medium incidence of typhoid fever, i.e., 10 to 100 cases in 100,000 populations per year; New Zealand, Australia and Europe have low to very low incidence (Crump et al., 2004). This suggests that Typhoid fever is strongly endemic in the regions of the World particularly in the developing nations and countries with low resource settings.

*Salmonella* belongs to the family of Enterobacteriaceae that includes the genera *Shigella*, *Escherichia*, and *Vibrio*. The genus of *Salmonella* contains two different species, *S. enterica* and *S. bongori*. *S. enterica* is further divided into six subspecies (*enterica, salamae, arizonae, diarizonae, houtenae* and *indica*) containing 2443 serovars. The agents that cause enteric fever are therefore *Salmonella enterica* subspecies *enterica* serovar *typhi* (commonly referred to as *S. enterica* serovar *typhi*) and serovars Paratyphi A, B and C. A serovar or serotype can be defined as a strain that has a unique surface molecule which is responsible for the production of specific antibody. Each serotype has subtle chemical differences in their antigenic region (Brenner et al., 2000).

*Salmonella typhi* has a combination of characteristics that make it an effective pathogen. This species contains an endotoxin typical of gram negative organisms, as well as the Vi polysaccharide antigen which is thought to increase virulence. It also produces and excretes a protein known as "invasin" that allows non-phagocytic cells to take up the bacterium, allowing it to live intracellularly. It is also able to inhibit the oxidative burst of leukocytes, making innate immune response ineffective. During the last decade, *Salmonella* species have been found to acquire more and more antibiotic resistance. The cause appears to be the increased and indiscriminate use of antibiotics in the treatment of Salmonellosis of humans and animals, and the addition of growth-promoting antibiotics to the food of breeding animals. Plasmid-borne antibiotic resistance is very frequent among *Salmonella* strains involved in pediatric epidemics. Resistance to ampicillin, streptomycin, kanamycin, chloramphenicol, tetracycline, ceftriaxone, cefotaxine, cefoperazone and sulfonamides is commonly observed; Colistin-resistance has not yet been observed. *Salmonella* strains should be systematically checked for antibiotic resistance to aid in the choice of an efficient drug when needed and to detect any change in antibiotic susceptibility of strains (either from animal or human source). Until 1972, *Salmonella typhi* strains had remained susceptible to antibiotics, including chloramphenicol (the antibiotic most commonly used against typhoid); but in 1972 a widespread epidemic in Mexico was caused by a chloramphenicol resistant strain of *Salmonella typhi*. Other chloramphenicol-resistant strains have since been isolated in India, Thailand and Vietnam.

Vaccination against typhoid fever caused due to *Salmonella Typhi* is essential for protection against these life-threatening disease due to increasing antibiotic resistance. It is also an important protective tool for people travelling into areas where typhoid fever is endemic. As the bacterium has the ability to acquire multi-drug resistance ability, antibiotics may not offer complete protection. Three types of typhoid vaccines have been made currently available for use till now: (1) Parenteral killed whole cell vaccine; (2) Oral live-attenuated vaccine; and (3) Typhoid-Vi capsular polysaccharide vaccine for parenteral use. Vaccines against typhoid fever were designed in early ages when the organism's cellular and molecular complexity was studied clearly. Initially parenterally administered whole cell *S. typhi* killed by heat-phenol-inactivation method was used as a vaccine, to be administered in two doses. Since the whole cell inactivated vaccines contain the 'O' antigen (endotoxin), they tend to produce local and general reactions in vaccinated individuals and these types of vaccines required a booster dose for every two years. Oral live-attenuated Ty21a vaccine are considered as second generation vaccines prepared with mutant *S. typhi* strain lacking adenylate-cyclase and AMP receptor protein and mutants auxotrophic for p-amino benzoate and adenine. These live attenuated vaccines reported poor efficacy and was found to be not suitable for administration of children's below 6 years of age. Additionally, a booster dose is also required for every 5 years. Subsequently, capsular Vi-polysaccharide of *S. typhi* was identified as a protective immunogen capable for eliciting adequate immune responses in humans and hence used as a potential vaccine candidate in routine immunization schedule. A dose of 25 µg/0.5 mL injection of purified capsular Vi-polysaccharide (ViPs) can produce maximum seroconversion i.e. fourfold rise in antibodies. However, the limitations of the Vi-polysaccharide vaccine has been reported in many clinical trials that native polysaccharide vaccine are incapable or do not produce secondary memory responses. This phenomenon is because of bacterial polysaccharides are T-cell independent in nature and hence are not capable to produce cell mediated immune responses. Therefore to overcome the said problem, polysaccharides of *S. typhi* and carrier proteins were further conjugated to form polysaccharide-protein molecules to make it T-cell dependent antigens. There are various factors that influence the coupling of polysaccharides and proteins which depend upon molecular weight of the ViPs and carrier proteins selected and activation of the functional groups. Low molecular weight polysaccharides can result in efficient coupling to carrier proteins. Different carrier proteins like tetanus toxoid, diphtheria CRM 197, the B subunit of the heat-labile toxin (LT-B) of *Escherichia coli*, the recombinant exoprotein A (rEPA) of *Pseudomonas aeruginosa* and Horseshoe rab Haemocyanin (HCH) have been mostly used for conjugation.

WO1996/011709 discloses an O-acetylated oligonucleotide or polygalactouronate pectin which is substantially identical to Vi polysaccharide subunit structure conjugated to a carrier protein tetanus toxoid wherein the carrier protein being derivatized with cystamine. This particular patent teaches to conjugate an identical polysaccharide but not Vi-polysaccharide to carrier protein with a different derivatizer that is cystamine, Subsequently, WO1998/026799 discloses an isolated lipo-polysachharide from *Salmonella Paratyphi* A, having removed its Lipid A through detoxification and retaining its O-acetyl content between 70% to 80% and then conjugated to a carrier protein tetanus toxoid through adipic acid dihydrazide (ADH). WO2000/033882 discloses a Vi-polysaccharide of the *Salmonella typhi* covalently bound to a protein *pseudomonas aeruginosa* (Vi-rEPA) conjugate through adipic acid dihydrazide. WO2007/039917 discloses an exogenous antigen of *Salmonella typhi* which is covalently/non-covalently bonded to a Heat Shock Protein.

WO2009/150543 describes a conjugated Vi-polysaccharide to be used as a vaccine composition against *Salmonella typhi* causing typhoid fever, wherein the Vi-polysaccharide is covalently conjugated to a protein selected from CRM197 or tetanus toxoid. The method of conjugation as disclosed in WO2009/150543 includes first simultaneously adding carrier protein which is preferably CRM197 or tetanus toxoid to a linker such as adipic acid dihydrazide (ADH), and a carbodiimide such as 1-ethyl-3(3-dimethylaminopropyl) carbodiimide (EDAC), to give a derivatized carrier protein in presence of a 2-(N-morpholino) ethane sulphonic acid (MES buffer). The weight ratio of the carbodiimide EDAC to the carrier protein is between 0.1 to 0.15. It also discloses that higher amounts of carbodiimide/protein ratios can cause aggregate formation. Derivatization of the carrier protein is followed by activation of the Vi-polysaccharide (ViPs) as well. The Vi-polysaccharide is also activated with a carbodiimide wherein various ratios of ViPs and carbodiimide (EDAC) are mixed to activate the Vi-polysaccharide. It is mentioned that Vi activation can be performed at room temperature within 2 minutes wherein higher ratios between 1.5:1 to 200:1 can be used. The derivatized carrier protein CRM197 or tetanus toxoid and the activated Vi-polysaccharide of *Salmonella typhi* is then reacted with each other to get the conjugated ViPs-CRM197 or ViPs-TT conjugate, followed by removal of the excess linker.

Safety and immunogenicity of ViPs conjugate vaccines in adults, teenagers and 2 to 4 year old children in Vietnam were evaluated by Zuzana Kossaczka et al in 1999. In this study the geometric mean level of anti-Vi-rEPA (conjugate vaccine) in the 2 to 4 year old children was higher than that elicited by Vi capsular polysaccharide vaccine in the 5 to 14 years old children. Re-injection of conjugate vaccine induced rise in antibody titers in 2 to 4 years old children (T-cell dependent). Konadu et al. (2000) prepared *S. paratyphi* A O-specific polysaccharide (O-SP) and coupled to tetanus toxoid. These conjugates elicited IgG antibodies in mice and the safety and immunogenicity of the conjugates was evaluated in Vietnamese adults, teenagers and 2-4 years old children. The study concluded that these experimental conjugates were safer and proven to elicit IgG antibodies in adults, teenagers and 2-4 years old children. The efficacy of *Salmonella typhi* ViPs conjugate vaccine in two to five year old children was evaluated by Feng Ying C et al. In this study the conjugate typhoid vaccine was found to be safe and immunogenic and had more than 90% efficacy in children two to five years old. Serum IgG Vi antibodies after six weeks of second dose levels increased 10 fold in 36 evaluated children. These cases were followed for a period of 27 months. No serious adverse reactions were observed in the study due to the vaccination. Effect of dosage on immunogenicity of ViPs conjugate vaccine injected twice in to 2 to 5 years old Vietnamese children was studied by Do Gia Canh et al. In this study dosage immunogenicity study of 5 µg, 12.5 µg and 25 µg of conjugate vaccine injected twice, six weeks apart was evaluated. This study also confirmed the safety and consistent immunogenicity of four lots of conjugate vaccine in this and previous trials. Novartis vaccine institute for global health carried-out three different dose-related formulations of ViPs-CRM197. They carried out different doses were 25 µg, 12.5 µg, 5 µg and 1.25 µg/dose. The GMT for these concentration at day 28 was 304 U (units), 192 U, 111 U and 63 U respectively. At day 28 GMT with 25 µg/dose elicited the highest antibody level (304 U) after single injection.

Although, the present state of the art includes conjugate vaccines with Vi-polysaccharide and a carrier protein, however, the existing native Vi-polysaccharide conjugate vaccines when tested in many human clinical trials revealed that these vaccines are safe and immunogenic in adults but failed to induce any protective immune response in children below 2 years of age. Therefore, this native *S. typhi* polysaccharide vaccine did not prove to find any particular solution against deadly *S. typhi* infections in children's less than 2 years of age which demands a new vaccine which could immunize children of age below 2 years against *S. typhi* infections responsible for causing typhoid. The age group of below 2 years of age is the most prone to infections by *Salmonella typhi* but there seems to be presently not available to the mankind any protective vaccine against *S. typhi* for infants below 2 years of age still now. As discussed above, various carrier proteins such as CRM-197, r-EPA, have been conjugated to Vi-polysaccharide, wherein the Vi-polysaccharide might not have been isolated from *S. typhi*, or being depicted from any other sources. Producing typhoid conjugate vaccines is therefore, specific to the particular carrier protein involved and the native polysaccharide involved in the conjugation process and the resulting conjugate vaccine. Each carrier protein-polysaccharide conjugation makes itself a different identity of conjugate vaccine. The prior arts disclosed in the area of typhoid conjugate vaccine, methodology and as well as those currently used, have their own drawbacks, which might be a possible reason behind not having any conjugate vaccine presently available which can protect children below 2 years of age.

It is also very much evident and well known in the current state of the art that, the present typhoid conjugate vaccines requires at least 2 or more injections with a time interval of 6-8 weeks to comprise a complete vaccination schedule A typhoid Vi capsular polysaccharide-tetanus toxoid (ViPs-TT) conjugate vaccine was made available to the public by BioMed, which required 2 injections of 5 µg each with a time interval of 6-8 weeks to complete a single vaccination schedule. However, this ViPs-TT vaccine also was not capable to immunize children below 2 years of age against *Salmonella Typhii*.

Hence, there exists a need of alternating conjugation methodologies, which would reduce costs, and the number of injections to only one injection capable of eliciting sufficient immune response and other associated technical concerns in the field of conjugation chemistry which would be more simpler, less time consuming, cost-effective and safe. An efficient vaccine must be capable of triggering a good immune response and must be applicable for use in infants especially below 2 years of age. The disclosure as set forth in this invention attributes to novel alternative methods of conjugating the Vi-polysaccharide along with the specific carrier protein tetanus toxoid (TT) in an inventive manner put-forth in this application which potentially overcomes the drawbacks of native polysaccharide vaccines and also current conjugation methodologies including other ViPs vaccines conjugated to carrier proteins. The Vi-polysaccharide-protein conjugate vaccine produced by this particular methodology as set forth in this patent application makes it more suitable for immunization in children and infants including less than 2 years of age with secondary memory responses producing high affinity antibodies against S. typhi infections, including humans of any age group. It is also another advantage of the invention put forth in this application that, the number of injections of typhoid conjugate vaccine to complete a vaccination schedule has also been reduced to only ONCE, which at the same time elicits a better immune response when compared to immune response generated by a vaccination schedule of 2 or 3 injections of typhoid conjugate vaccine being practiced earlier. Single injection of typhoid conjugate vaccine is always preferable for infants and children since it would reduce, additional visits to the clinic, pain suffered by a child or infant for repeated injections for vaccination. It is already reported that, 40% of injections worldwide are administered with un-sterilized, reused syringes and needles, and especially in the targeted developing countries, this proportion is more than 70%, exposing millions of people to infections wherein pathogens enter the tissues of the body during an injection. Furthermore poor collection and disposal of dirty injection equipment, exposes healthcare workers and the community to the risk of needle stick injuries. Unfortunately in some countries, unsafe disposal also lead to re-sale of used equipment on the black market. Open burning of syringes is unsafe under WHO, yet half of the non-industrialized countries in the World, follow this practice. ("Injection safety", Health Topics A to Z. World Health Organization. Retrieved May 9, 2011). Unsafe injections cause an estimated 1.3 million early deaths each year. (M. A. Miller & E. Pisani. "The cost of unsafe injections". Bulletin of the World Health Organization 77 (10): 1808-811). Although, to improve injection safety, the WHO recommends certain alternatives to injections subject to availability, or else controlling and regulating the activity of health care workers and patients, vaccinees, by ensuring the availability of equipment and supplies aided with managing waste safely and appropriately; these measures are not always possible to be observed absolutely. In such circumstances, a combination of Typhoid conjugate and measles vaccine in one SINGLE shot will definitely play a substantial role in decrease of worries pertaining to injection safety in national immunization programs. Many countries do have legislation or policies that mandate that healthcare professionals use a safety syringe (safety engineered needle) or alternative methods of administering medicines whenever possible, however reduction in the number of injections for ensuring protection against Typhoid and Measles in one single injection in infants surely indicates high compliance from a public health perspective since where there was at least 3 injections required earlier to inject typhoid (2 injections minimum) and measles (one injection) vaccine, now the same is accomplished by only ONE injection.

OBJECTS OF THE INVENTION

Primary object of the invention is development of a vaccine formulation for prophylaxis and treatment of Salmonella typhi infections in humans so that the T-independent polysaccharides can be made T-cell dependent thereby facilitating to produce efficient immune responses in children of all age groups especially below 2 years of age and also including adults as well.

Another object of the invention is to provide a vaccine composition against fever caused due to S. typhi with suitable conjugate polysaccharides as the vaccine antigen that would confer protection to children below 2 years of age.

One objective of the invention is to provide a fed-batch method of production of Vi capsular polysaccharide.

One more objective of the invention is to provide methods of conjugation of Vi capsular polysaccharide with or without size reduction to a carrier protein.

Yet another objective of the invention is to provide alternative methods effective conjugation methodology in a reduced time through size-reduction of ViPs of Salmonella typhi prior to conjugation with carrier protein thereby increasing the percentage of conjugation between the Vi polysaccharide and carrier protein.

Yet another object of the invention is to provide a method of conjugation for Vi capsular polysaccharide of Salmonella typhi and a carrier protein tetanus toxoid as final polysaccharide conjugated bulk and finished vaccine with or without a linker molecule.

A further objective of the invention is to provide immunogenic vaccine formulations comprising coupled polysaccharide-protein conjugates of Vi-polysaccharide-proteins in appropriate single dose and multidose vials in infants and adults to be administered at appropriate concentrations effective to confer prophylaxis against S. typhi.

SUMMARY OF THE INVENTION

According to one embodiment of this invention, cultivation and processing of Salmonella typhi Vi-polysaccharide is disclosed. It is further purified through several downstream processing steps to obtain pure Vi-polysaccharide.

According to one other embodiment of this invention, method of conjugation of pure Vi-polysaccharide to conjugate with protein tetanus toxoid is disclosed in the presence of a linker molecule Adipic Acid Dihydrazide (ADH). The yield of pure resultant ViPs-TT conjugate is as high as 70%-80%.

According to one other alternative embodiment of this invention, method of conjugation of Vi-polysaccharide to conjugate with protein tetanus toxoid is disclosed without presence of any linker molecule. The yield of pure resultant ViPs-TT conjugate without linker is as high as 70%-80%.

A further embodiment of this invention discloses stable formulations of ViPs-TT conjugate vaccine in appropriate concentrations of ViPs-TT with or without 2-phenoxyethanol as preservative with ViPs-TT to ensure, a complete vaccination schedule through one injection only.

One another embodiment of this invention provides, clinically established experimental data of the stable ViPs-TT conjugate vaccine formulation evidencing strong seroprotection and eliciting the desired immunogenicity against *Salmonella typhi* infections in humans including infants below 2 years of age (6 months to 2 years), as well as subjects in other age groups through only one injection comprising a complete vaccination schedule.

DETAILED DESCRIPTION OF THE INVENTION

Figure 1:
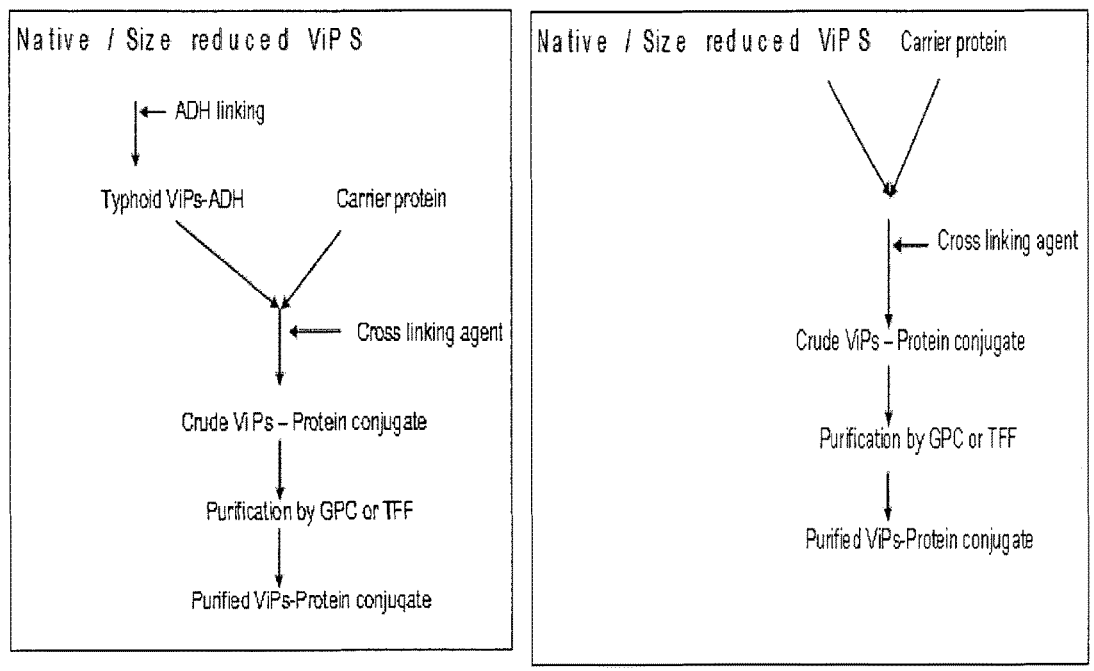
FIG. 1: General flow diagram of ViPs production and conjugation with linker ADH (left side) and without linker (right side).

*Salmonella typhi* are grown in suitable medium and the actively grown cells were transferred into the fermenter containing pre-sterilized medium. Initially, batch mode fermentation process is carried out and once the cultures reaches early stationary phases, a feed medium containing high concentration of carbon source was pumped into the fermenter incrementally. Fed-batch mode fermentation process is carried out till the desired optical density was obtained. The cultures are harvested by inactivating with low concentration of formalin and then centrifuged to obtain cell supernatant. Hexadecyltrimethylammonium bromide (Cetavlon) is added to the cell supernatant to precipitate the crude Vi-polysaccharide from host cell components. Sequential purification steps i.e ethanol precipitations, concentration and diafiltration using different molecular weight cut-off membranes and sterile filtration techniques were carried out to isolate purified Vi-polysaccharide from host cell impurities like nucleic acids, proteins and lipo-polysaccharides.

The factors that influence the coupling of polysaccharides and proteins depend upon molecular weight and activation of the functional groups. Low molecular weight of polysaccharides can result in efficient coupling. Different proteins like tetanus toxoid, diphtheria CRM 197, the B subunit of the heat-labile toxin (LT-B) of *Escherichia coli*, the recombinant exoprotein A (rEPA) of *Pseudomonas aeruginosa* and Horseshoe rab Haemocyanin (HCH) have been mostly used for conjugation. Determining molecular sizes of polysaccharides and polysaccharide-protein conjugates of bacterial polysaccharides is an important aspect in designing conjugate vaccines. The assessment of physico-chemical characteristics of polysaccharide-protein conjugate plays important role in eliciting specific immune responses. Determination of the molecular size of the polysaccharide before and after conjugation results in efficient conjugation. The two important critical quality control tests employed after conjugation and purification are the 'polysaccharide (PS) to protein ratio' and the 'percent non-conjugated polysaccharide (Free polysaccharide)'.

Podda et al. (2010) reported the epidemiology and significance of vaccination in the children below two years of age. The currently available vaccines have some relevant limitations and hence cannot be used in children under two years of age, an age group affected by a significant burden of typhoid disease. Introduction of a conjugate vaccine is expected to be an effective tool for efficient immunization of all age groups yet there is no experimental data available at present which would enable vaccination of typhoid conjugate vaccine below 2 years of age. This invention, relies on its unique conjugation methodology of the ViPs-TT conjugate vaccine having an advantage of making it possible to vaccinate children or infants under two years of age to be prevented from *Salmonella typhi* infections that causes typhoid fever in this tender age group which is accordingly supported by experimental clinical trial data, and also reduces the number of injections to accomplish a complete vaccination schedule through only one dose of the typhoid conjugate vaccine in infants below 2 years of age.

Example 1: Cultivation and Processing of *S. typhi* Vi Polysaccharide

The strain *Salmonella typhi* (Ty2) was obtained from Dr. John Robbins, National institutes of Child Health and Human Development (NICHD), USA. The culture received form NICHD, USA was confirmed and identified as *Salmonella* serovar *typhi* by identification of the following characteristics: gram staining, glucose positive without gas formation, $H_2S$ positive on a Xylose Lysine Deoxycholate agar (XLD agar), and positive serology with Vi-polysaccharide. The purity of the strain was confirmed on different selective media such as, Bismuth Sulfite Agar (BSA), Triple Sugar Iron (TSI) agar. The purity of the strain was confirmed on different selective media such as Xylose Lysine Deoxycholate agar (XLD agar), Bismuth Sulfite Agar (BSA), Triple Sugar Iron (TSI) agar.

*Salmonella typhi* Ty2 was grown on Soyabean Casein Digest (SCDM) medium at 37±1° C., for 12 hours. The bacterial culture was centrifuged and the pellet was re-suspended in sterile glycerol (50%). 0.5 mL aliquots of the glycerol suspension in 1 mL cryovials were prepared and stored at −70° C. Viable cell count of the master seed was also carried out. The contents of cryovial of the Master seed lot was inoculated into SCDM broth and incubated at 37±1° C. for 12 hours. The bacterial culture was centrifuged and the pellet was re-suspended in sterile glycerol (50%). Viable cell count was carried out. Aliquots of the glycerol suspension in cryovials were prepared and stored at −70° C. The Master and Working cell banks were characterized by grams staining, utilization of glucose (Durham's method), oxidase test, agglutination test and viable cell count. This was plated on Tryptone Soya Agar (TSA) and incubated at 37° C. for 48 to 72 hours. Colony count was performed using colony counter.

1.1. Fermentation Process:

Inoculum Development:

The contents of one cryovial of the working seed lot was removed from the freezer and thawed at room temperature using a water bath. One cryovial from working cell bank of *Salmonella typhi* was inoculated into 10 mL Soybean Casein Digest Medium (SCDM) and cultured at 37±1° C. for 12 hours (Stage-I), transferred to two flasks each containing 50 mL SCDM at 37±1° C. for 12 hours (Stage-II) and finally transferred to four flasks each containing 400 mL SCDM and incubated at 37±1° C. for 12 hours (Stage-III). At every stage of culture transfer, purity and morphological characteristics was checked by gram staining. The OD was checked at 600 nm. The OD of the *Salmonella typhi* culture recorded at different stages of seed growth varied from 1.2 to 3.8.

Batch Mode Fermentation:

TABLE 1.1

| Fermentation parameters and specification limits | |
|---|---|
| Parameters | Ranges |
| pH | 6.9 ± 0.2 |
| Dissolved oxygen | 70-90% |
| Stirrer speed | 250 ± 10 rpm |
| Temperature | 37 ± 2° C. |
| Air flow | 0.5 ± 0.1 VVM (Volume per volume per minute) |

Initially 85 L of SCDM was prepared in 100 L S.S vessel and transferred to the fermentor. This was sterilized in situ at 121° C. for 15 minutes. The medium was cooled to 37° C. At this stage supplement mix was pumped into the fermentor through the addition port. To maintain pH, 50% ammonia solution in a bottle was connected to the addition port as a nitrogen source. The seed inoculum was transferred into the fermentor and the fermentation process was carried out at a pH of 6.9±0.2, temperature of 37±2° C. and the Dissolved Oxygen is maintained at 70-90%. for a period of up to 22 to 24 hours. The growth was checked by taking the OD values at 600 nm initially at 0 hour and at every 2 hours up to 24 hours.

Fed Batch Mode Fermentation:

Fed batch fermentation process for *S. typhi* resulted in increased Vi polysaccharide production. Stage III cultures with an $OD_{600}$ of 3.8 was ideal for fermentation. The pH was maintained at 6.90 and dissolved oxygen level was between 40% to 60%. To the early stationary phase culture the feed medium containing carbon source along with inorganic salts and minerals was pumped incrementally into the fermenter throughout the fermentation process. The fed batch fermentation process adopted herein to increase biomass by feeding with a solution containing glucose at a range of 1 to 2 mg/mL concentration. The pH was maintained in the range of 6.90 to 7.20 and dissolved oxygen level was maintained between 40%-60%. Ammonia solution (50%) was supplied as a nitrogen source along with the feed medium. Foaming was controlled by pumping antifoam solution through the addition port aseptically. The optimal pH maintained was 7.2 using 10% $NH_4OH$ and dissolved oxygen concentration was maintained at 35% air saturation. Glucose level was monitored every 30 minutes, and through the fed-batch process the glucose concentration was maintained at about 1 g/L throughout the process.

Process was continued up to 24 hours and then the bacterial culture were inactivated with 0.5% formaldehyde and kept under mild stirring in chilled condition (below 15° C.). The growth was checked by taking the OD values at 600 nm for 0 hr and every 2 hours for 24 hours. This feeding strategy resulted in an increase in the biomass in terms of optical density to about 120 to 130. The increased biomass translated into a greater Vi polysaccharide production which achieved a final yield of Vi-polysaccharide obtained in the fed batch culture of approx 1000 mg per liter in the present process from which 400 mg of purified ViPS per liter was finally obtained, after completion of downstream processing. Thus, Fed-Batch mode of cultivation resulted in a final yield of at least 40%.

1.2. Downstream Process of Purified Vi Polysaccharide Bulk (VIPs):

Fermentation cell supernatant is subjected to different steps of purification to isolate purified Vi-polysaccharide. Vi-polysaccharide consists of partly 3-O-acetylated repeated units of 2-acetylamino-2-deoxy-d-galactopyranuronic acid with α-(1→4) linkages. Hence the determination of O-acetyl content could be correlated to the amount of Vi-polysaccharide. The final pure Vi-polysaccharide fraction should contain 2 mM of O acetyl per gram of Vi-polysaccharide (WHO TRS 840). The supernatant normally contains large amount of proteins, nucleic acid and lipopolysaccharides. Filtration techniques play an important role in downstream processing in purification of bacterial polysaccharides from host cell impurities. Retention of the desired molecule from the dissolved substances is done on the basis of size; higher sized particles will be retained at the surface and those lower than the nominal weight limit (NMWL) of the membrane flow out in the permeate (Jagannathan et al., 2008). 100 kDa cut-off membrane cassettes were used at initial step of cell supernatant concentration and 300 kDa cut-off membrane cassettes at final concentration step and diafiltered using sterile water for injection (WFI).

Cell Separation:

The harvested culture was centrifuged in a bowl centrifuge at 9000 rpm (8000 g) for 30 minutes at 4° C. The supernatant was collected in sterile vessels. A sample was taken from the supernatant and assayed for O-acetyl content.

Concentration and Diafiltration:

The supernatant was diafiltered by using tangential flow filtration (TFF) system using 100 kDa membrane. The supernatant was concentrated to 1/10th of the original volume and further diafiltered with water for injection (WFI) till the required concentrate was obtained. O-acetyl content of the concentrate was assayed.

Cetrimide Precipitation:

To the concentrate 0.4 M cetrimide was added and incubated at (5°±1° C.) for 3±1 hours. The contents were centrifuged at 9000 rpm for 30 minutes at 4° C. The pellet collected was suspended in the required volume of 1 M NaCl. The O-acetyl content of the pellet suspension was determined.

Ethanol Precipitation:

One volume of ethanol and 2% of sodium acetate were added to the resuspended cetrimide precipitate; the contents were stirred for 20±5 minutes using a magnetic stirrer. Contents were centrifuged at 4200 rpm (8000 g) for 30 minutes at 4° C. The supernatant was collected into a sterile bottle and the pellet was discarded. To the supernatant, two volumes of ethanol were added (100%) under continuous stirring for a period of 60±10 minutes. 2% of sodium acetate was added to the above content under continuous stirring. After 1 hour of incubation, the contents were centrifuged at 4200 rpm (8000 g) for 30 minutes at 4° C. The supernatant was discarded; pellet was suspended in sterile cool WFI and transferred to sterile bottle. Sample was checked for O acetyl content. Filtration: The concentrated ViPs bulk was passed through 0.22μ capsule filter (Sartopore, Sartorius). This sterile filtered purified bulk of ViPs was assayed for O-acetyl content. The ViPs bulk thus obtained was re-extracted with cetrimide and precipitated with ethanol. Finally, the bulk was concentrated and diafiltered using a 300 kDa cassette (known as concentrated bulk) as mentioned above. The O-acetyl content was assayed after each process. The following O-acetyl contents at different steps of downstream processing, as given in the table 1.2 below was obtained. The O-acetyl content was analyzed by Hestrin method as described below.

Assay for O-Acetyl Content:

Determination of O-acetyl content was performed by the method of Hestrin. (Hestrin, 1949). The amount O-acetyl in the sample was proportional to the amount of Vi-content expressed in mg/mL. 0.5 mL of 3.6 N HCl and 1 mL of alkaline hydroxylamine solution were added to the test samples and mixed thoroughly. The mixture was kept at room temperature for 2 minutes and 0.5 mL of ferric chloride solution added and mixed well. The absorbance was measured at 540 nm. The O-acetyl content was calculated as follows:

$$\text{O-acetyl}(\mu\text{moles/mL}) = \frac{\text{Test } OD \times \text{Standard concentration} \times \text{dilution factor}}{\text{Standard } OD}$$

Factor for O-acetyl to $Vi$ content conversion =

$$\text{O-acetyl}(\mu\text{moles/mL}) \times 0.294$$

$$(25/0.085/1000) = Vi \text{ content(mg/mL)}$$

Figure 2:
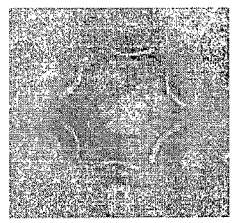
FIG. 2: Serological identification test of Vi polysaccharide.

The final sterile filtered (0.22 Vi-polysaccharide bulk is lyophilized in a low temperature vacuum dryer (Lyophilizer FTS system). The lyophilized powder was tested for serological identification by Ouchterlony method, moisture content, protein content, nucleic acids, molecular size distribution and bacterial endotoxin content. In the present study purified Vi-polysaccharide and corresponding homologous antisera were filled in the wells until the meniscus just disappears. The gel plate was incubated in a humidity chamber. The precipitin lines were observed by naked eye when the plate was seen against a bright light back ground. A photograph of the same is shown in FIG. 2, showing a clear precipitin are observed.

The molecular size distribution of Vi-polysaccharide was determined by using gel permeation column with Sepharose CL-4B as stationary phase. Fractions were collected after void volume (Vo) corresponding to kDa 0.25 and pooled together. 75% of poly-saccharide eluted at kDa of 0.25. The molecular size distribution of S. typhi Vi-polysaccharide bulk is given in the Table 4.5 below. Characterization of Vi revealed it to have 1% nucleic acids, 0.3% of proteins and an O-acetylation of level of 86% by H-NMR Results of dried ViPs bulk obtained for a single batch are tabulated in the table 1.2 below:

TABLE 1.2

Results of dried Vi-polysaccharide bulk

| Tests | Results |
|---|---|
| Serological identification (Ouchterlony) | Clear precipitin arc was observed |
| Moisture content | 1.80% |
| Protein | 2.5 mg/g of Vi polysaccharide powder |
| Nucleic acids | 5 mg/g of Vi polysaccharide powder |
| O-acetyl content (Hestrin) | 2.1 mmoles/g of Vi polysaccharide powder |
| Molecular size distribution | 75% of polysaccharide eluted at 0.25 kDa |
| Endotoxins | Less than 150 EU/μg of Vi-polysaccharide powder |

The above results met all the requirements of WHO TRS 840, British pharmacopeia (2010) and Indian pharmacopeia (2010) standards. The requirements of WHO TRS 840 (1994) were considered as standard specifications in present study. The standard requirements of WHO are proteins 10 mg/g, nucleic acids 20 mg/g, O-acetyl content not less than 2 mmol/g of Vi-polysaccharide, molecular size of 50% polysaccharide should elute before 0.25 kDa, Identity by immune precipitation method and sterility test passing. Accordingly to British and European pharmacopeia (2007), the dried Vi-polysaccharide specifications are: protein 10 mg/g, nucleic acids 10 mg/g, O-acetyl groups 2 mmol/g, Not less than 50 percent of the polysaccharide to be found in the pool containing fractions eluted before kDa 0.25, identification using a immunoprecipitation method, and bacterial endotoxin test. These specifications are similar to the WHO TRS 840, British pharmacopoeia (2010) and Indian pharmacopoeia (2010).

Example 2: Conjugation Methodology

Efficient methods of conjugation of the purified Vi polysaccharide (VIPs) to a carrier protein selected from any bacterial protein or a viral protein, such as diphtheria toxoid, tetanus toxoid, *Pseudomonas aeruginosa* toxoid, pertusis toxoid, *Clostridium perfringens* toxoid, *Pseudomonas* exoprotein A, CRM197 are disclosed in this present invention. Preferably the purified ViPs is conjugated to tetanus toxoid in this present invention. High yield of conjugation are achieved employing various alternative conjugation methodologies. The purified ViPs may be subjected for size reduction prior to conjugation. In the present invention, efficiency of conjugation using either high molecular size (non size reduced) or low molecular size (size-reduced) ViPs was conducted in both the methodologies to achieve high yields of purified ViPs-TT conjugate. For conjugation with high molecular size ViPs and tetanus toxoid, the concentration of ViPs (non-size reduced) in the final reaction mixture shall lie in the range of 1 mg/ml to 10 mg/ml to obtain the desired yields of ViPs-TT conjugate up to 70%-80%, whereas for conjugation of low molecular size ViPs and tetanus toxoid, the concentration of ViPs (size reduced) in the final reaction mixture shall lie in the range of 5 mg/ml to 10 mg/ml to obtain the desired yields of ViPs-TT up to 70%-80%. Alternative methods of size reduction of the purified ViPs is disclosed in the following sections.

The novelty of the present invention is modification of the Vi polysaccharide and activating them with a linker or without a linker molecule in presence of cross linking agents. According to the present invention, there lies no requirement to activate conjugate proteins. Conjugation between activated polysaccharides and carrier proteins takes place in presence of cross linking agents such as EDAC. WO2009/150543 teaches derivatizing the proteins for conjugation, in which the Vi-polysaccharide was isolated from C. freundi and further conjugated with CRM197 and/or tetanus toxoid as carrier proteins. In their study Vi and EDAC were mixed at appropriate molar ratio (EDAC/Vi) of 0.9-1.4, alternatively CRM197 and/or TT were derivatized with treatment with ADH and EDAC. Vi was conjugated to CRM197 and TT separately and the conjugation mixture was purified using Sephacryl S-1000; fractions were analysed by SDS-PAGE and those which did not contain free protein were collected (Micoli et al., 2011). However, according to WO2009/150543, the excess linker has been removed by dialysis, whereas in the present invention, Vi-polysaccharide was optionally subjected for size reduction (homogenization or by microwave method) and then conjugation has been achieved optionally coupled to the linker molecule or without any linker molecule at all. Hence, wherein linker molecule has not been used, there is no requirement of additional step of removing excess linker molecule. Additionally, in the process involving conjugation with the linker molecule, excess linker was removed by desalting and diafiltration unlike dialysis as mentioned in WO2009/150543.

Figure 3:
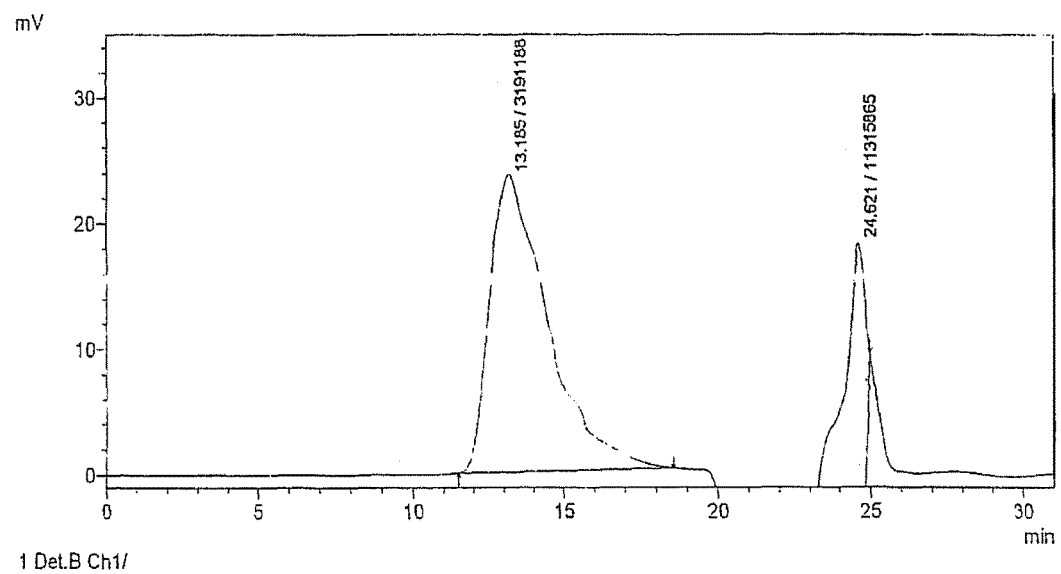
FIG. 3: HPLC (RI Detector) for Typhoid native Vi-polysaccharide, the HP-GPC column profile of the purified Vi-polysaccharide was analyzed by RI detector. The peak at 13.185 minutes represents native Vi-polysaccharide, which signifies molecular weight of ~900 kDa.
Figure 4:
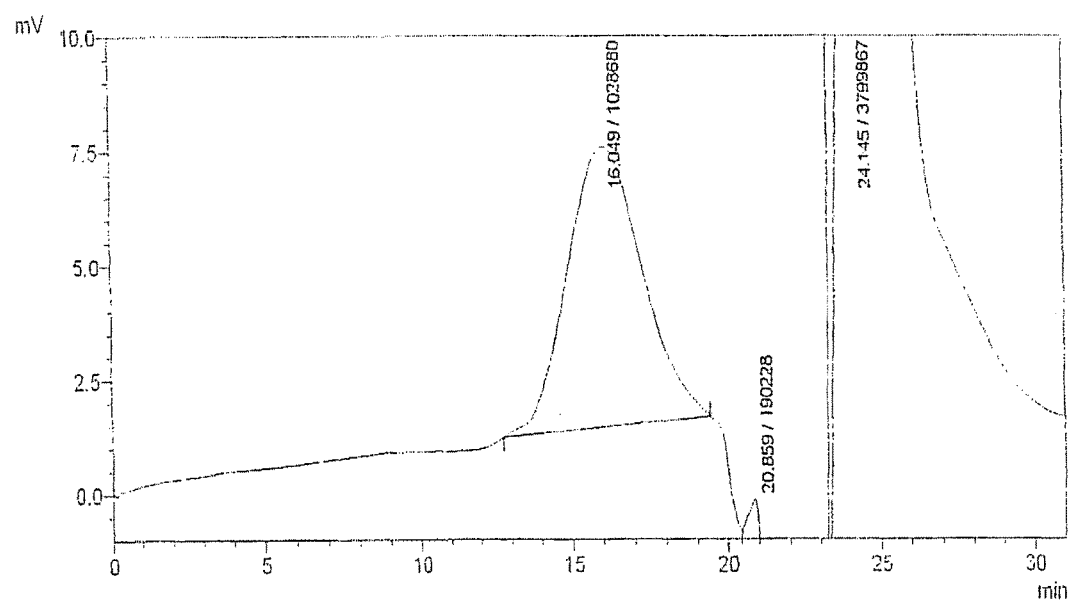
FIG. 4: Size reduced ViPs using homogenizer for about 45 passes. The HP-GPC column profile of the size reduced Vi-polysaccharide was analyzed by RI detector. The peak at 16.04 minutes represents size reduced Vi-polysaccharide, which signifies molecular weight of ~200 kDa.

2.1. Size Reduction of ViPs Using High Pressure Homogenization:

ViPs is a very large molecule of nearly 1000 kDa. Therefore, the size of the molecule is preferably reduced to approximately one fourth of the large molecule for enabling conjugation with carrier proteins including Tetanus Toxoid at low concentrations. Therefore, the ViPs at a concentration of 5-7.5 mg/ml was subjected to high pressure homogenization at 1500 bar at 2-8° C. and the same activity was repeated for at least 45 passes. The molecular size of the reduced ViPs was thereafter verified through Size Exclusion-Gel Permeation Chromatography as shown in corresponding figures. The retention time of ViPs before size exclusion was 13.185 minutes (FIG. 3), whereas after size exclusion chromatography the retention time of ViPs was eluted at 16.04 minute (FIG. 4), which signifies that the ViPs has been reduced to a corresponding molecular size of approximately 200 kDa. The O-acetyl content of the size reduced ViPs remains the same after homogenization treatment verified by hestrin method. Thereafter, the size reduced ViPs was subjected further to subsequent conjugation steps as discussed in the following sections.

Figure 5:
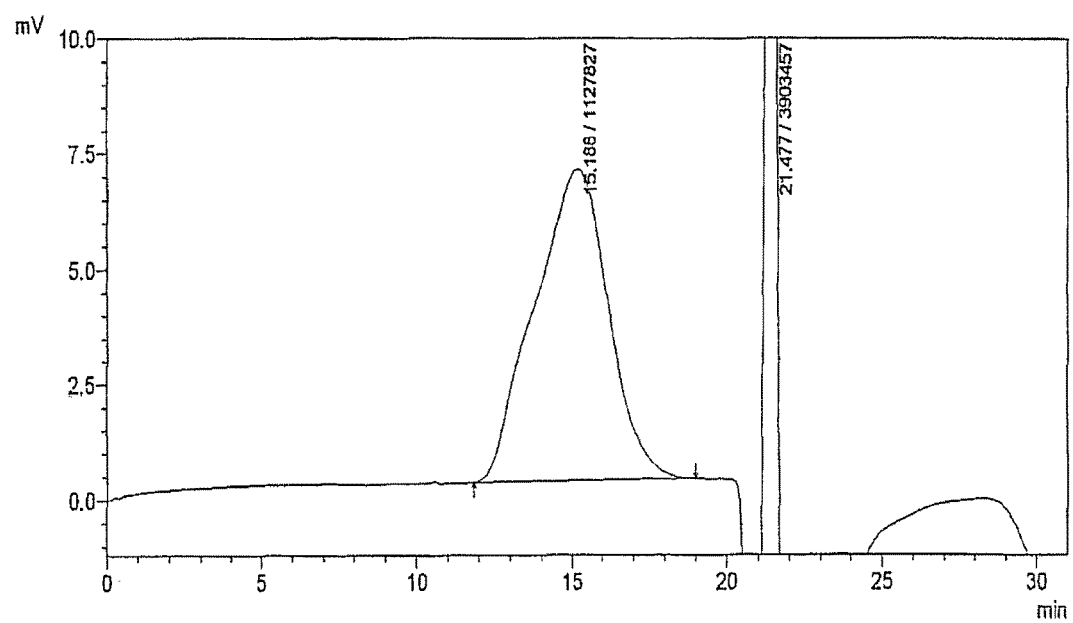
FIG. 5: Size reduced ViPs using microwave oven. The HP-GPC column profile of the size reduced Vi-polysaccharide was analyzed by RI detector. The peak at 15.18 minutes represents size reduced. Vi-polysaccharide, which signifies molecular weight of ~250 kDa.

2.2. Size Reduction of ViPs Using Microwave Oven:

Another method of size reduction of ViPs prior to conjugation was done using micro-wave oven. The ViPs at a concentration of 5-7.5 mg/ml in a glass bottle was put inside a micro-wave oven at 50%-100% power for 5-10 minutes. The micro waves generated inside the oven is responsible for cleaving the glycosyl bonds of long chains of the Vi polysaccharide to reduce it to shorter molecules required to conjugate them to carrier protein. The molecular size of the reduced ViPs was thereafter verified through Size Exclusion-Gel Permeation Chromatography as shown in the corresponding figures. The retention time of ViPs before size exclusion was 13.185 minutes (FIG. 3) whereas after size exclusion chromatography the retention time of ViPs was eluted at 15.18 minute (FIG. 5), which signifies that the ViPs has been reduced to a corresponding molecular size of approximately 250 kDa. The O-acetyl content of the size reduced ViPs remains the same after microwave treatment verified by hestrin method. Thereafter, the size reduced ViPs was subjected further conjugation techniques as discussed in the following sections.

2.3. Conjugation of Vi Polysaccharide and Tetanus Toxoid with a Linker

The purified Vi polysaccharide (either size reduced or non-size reduced) were partially de-O-acetylated in presence of sodium bicarbonate, and coupled with ADH using EDAC mediated reaction at a range of pH 6.0-7.5. The reaction was maintained at 2-8° C. with mild stirring. After incubation, the reaction mixture was quenched by bringing the pH to 8.0 using phosphate buffer-EDTA buffer and further dialyzed using low molecular cut-off membranes with initially phosphate and then followed by MES buffer. The final mixture is concentrated and tested for O-acetyl content, Vi Ps-ADH ratio, free ADH.

The tetanus toxoid was concentrated and diafiltered with MES buffer using low molecular weight cut off membrane. The final concentrated Tetanus toxoid is tested for protein content. For conjugation the modified Vi-polysaccharides and proteins are coupled in the presence of carbodiimide condensation using EDAC. The final coupled molecules are concentrated and diafiltered using a 1000 kDa cut-off membrane preferably PES (polyether sulphone) membrane, followed by continuous buffer exchange using 20 diavolumes of phosphate buffered saline. The retentate which contained purified ViPs-TT is checked for polysaccharide-protein ratio which shall be within the ratio of 0.5% to 1.5%, Vi-content, protein content and molecular size distribution. Final conjugate bulk was sterile filtered using 0.22µ membrane and stored at 2-8° C.

Optionally, the final coupled molecules are concentrated and diafiltered using a 1000 kDa cut-off membrane preferably PES (polyether sulphone) membrane, using phosphate buffered saline and then loaded into a gel permeation column (Sepharose cross linked beads). Fractions collected which are within the ratio of 0.5% to 1.5% were pooled together, concentrated and checked for polysaccharide-protein ratio, Vi-content, protein content and molecular size distribution. Final conjugate bulk was sterile filtered using 0.22µ membrane and stored at 2-8° C.

The molecular size distribution of the present invention, Vi polysaccharide conjugate bulk is given in the Table 2.1. The molecular size of the ViPs-TT conjugate obtained in the present invention is 0.3 kDa; when compared with the results obtained in earlier studies of the conjugate ViPs-TT the molecular size distribution of the given conjugate was <0.1 kDa. This means, molecular size distribution of 0.3 kDa indicates optimal filterable size which allows proper filtration of the ViPs-TT, at the same time providing better immunogenicity to the conjugate vaccine as compared to other lower molecular size distribution(s) provided in the prior arts. Bigger molecular size signifies better immunogenicity, whereas it is also essential to limit the molecular size, at appropriate size which would allow filtration of the ViPs-TT. Therefore, due to this molecular size distribution of 0.3 kDa only ONE single injection of the typhoid conjugate vaccine as laid down in this present invention, is sufficient to comprise a complete vaccination schedule against typhoid fever caused by *Salmonella typhi*. Prior art prescribes more than one injection, preferably three doses in case of lower molecular size distribution conjugate vaccines against typhoid fever.

Determination of total and free (unbound) Vi polysaccharide was measured by HPAEC-PAD analysis. In the present methodology the Vi conjugate has yielded 75% of Vi polysaccharide conjugate as eluted at kDa 0.30 thereby giving better polydispersity, and yielded Vi content 0.56 mg/ml, free ViPs 5%, protein content 0.25 mg/mL, Vi Ps-Protein ratio-1.05, free protein peak not detectable and sterility was found be acceptable (Refer Table 2.1). The present methodology was performed with an initial batch size of 10 gms of ViPs, which yielded 8 liters of ViPs conjugate bulk at a Vi conjugate concentration of 0.9 mg/ml-1.0 mg/ml which yielded 7-8 gms of ViPs-TT conjugate, thereby giving an yield of 70%-80%.

TABLE 2.1

Results of the ViPs-TT conjugate bulk with linker

| Tests | Results (in ranges) |
|---|---|
| Molecular size distribution | 75.7% of polysaccharide eluted at kDa 0.3 |
| Conjugate Vi content | 0.9 mg/ml-1.0 mg/ml |
| Free Vi Ps | 3%-6%. |
| Protein content | 0.78 mg/ml-0.9 mg/ml |
| Vi Ps/protein ratio | 1.1 |
| Free protein | Peak was not detectable at $17^{th}$-$18^{th}$ minute in HPLC UV (280 nm) chromatogram. Free protein is absent |
| Sterility | No growth was observed |

Figure 6:
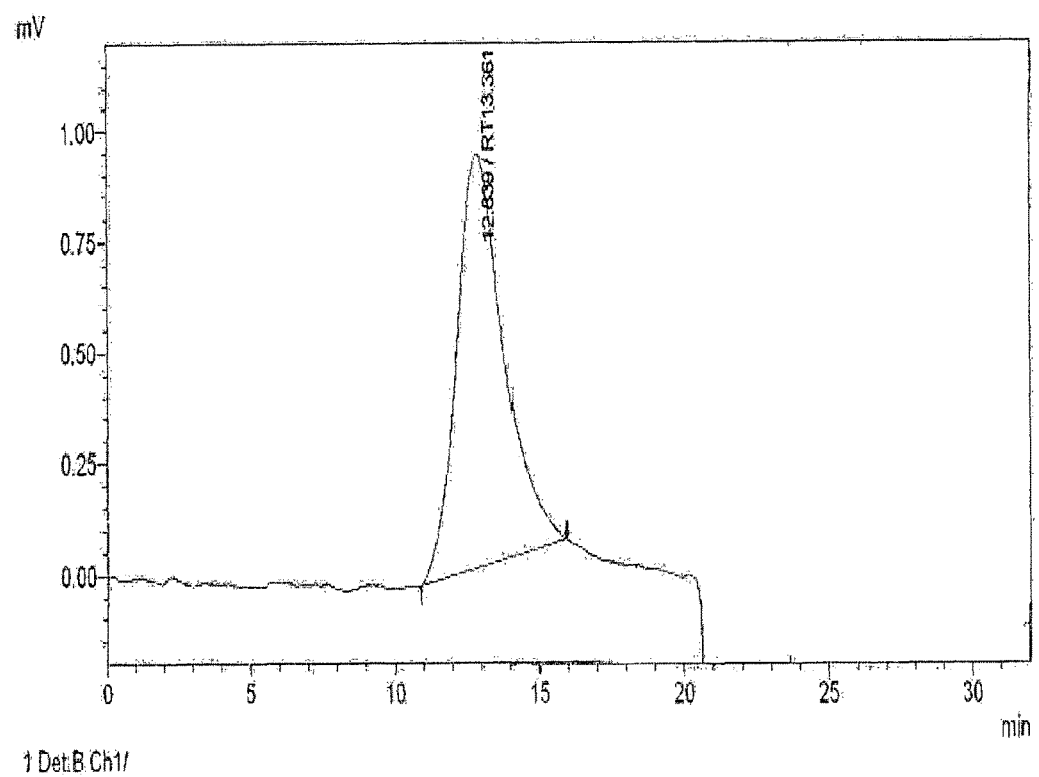
FIG. 6: HPLC (RI) for ViPs-TT conjugate bulk. HPLC Profile of the Vi-polysaccharide-Tetanus toxoid conjugate was detected by RI detector using HP-GPC column. The peak at 12.83 minutes represents conjugate ViPs-TT without linker molecule.
Figure 7:
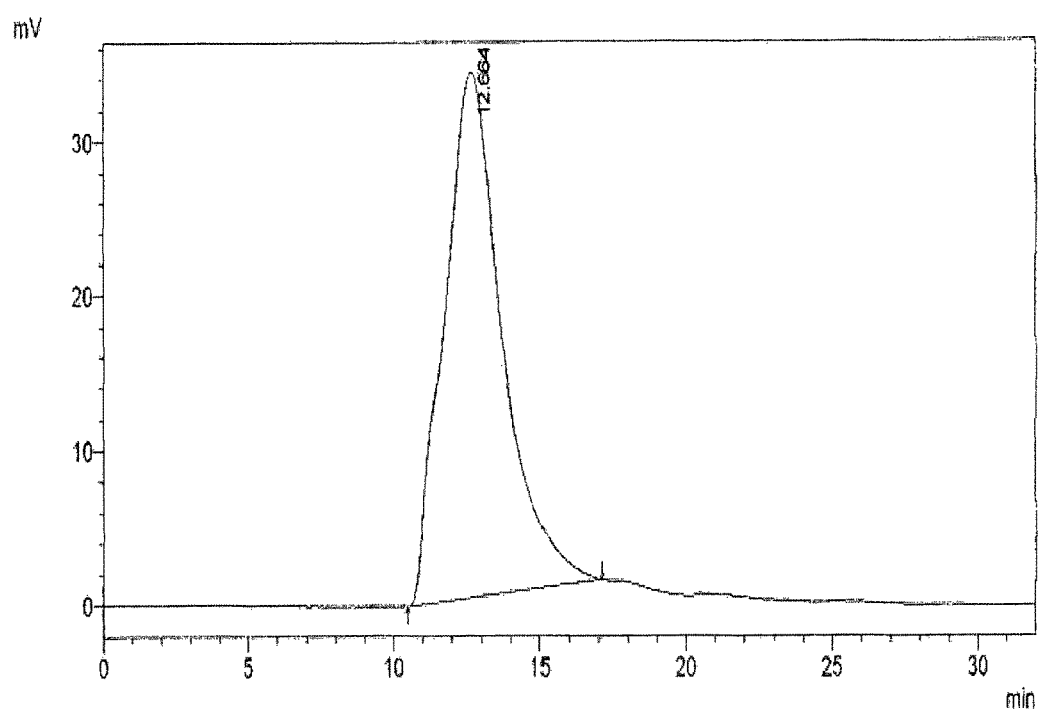
FIG. 7: HPLC (UV) for ViPs-TT conjugate bulk. HPLC Profile of the Vi-polysaccharide-Tetanus toxoid conjugate was detected by UV detector using HP-GPC column. The peak at 12.66 minutes represents conjugate ViPs-TT without linker molecule.

FIGS. 6 to 7 represents HPLC Chromatograms of Vi-polysaccharide, and ViPs-TT Conjugate bulk at different stages with linker. All the given HPLC profiles clearly demonstrate the conjugation efficiency of the present methodologies.

The conjugation methodology with linker molecule ADH to obtain a purified ViPs-TT conjugate vaccine antigen for preparation of a conjugate vaccine formulation against typhoid fever caused by *Salmonella typhi* as described above can be summarized with the following steps:

a. Fed-batch mode of cultivation to obtain purified ViPs with a feed medium, the said feed medium comprising feeding with a solution containing glucose at a range of 1 to 2 mg/mL concentration at a pH maintained in the range of 6.90 to 7.20 and dissolved oxygen level maintained between 40%-60%, wherein ammonia solution (50%) was supplied as a nitrogen source along with the feed medium;

b. optionally size reduction of ViPs, wherein the ViPs at a concentration of 5-7.5 mg/ml is subjected to high pressure homogenization at 1500 bar at 2-8° C. and the same activity repeated for at least 45 passes or by a microwave oven so that to a corresponding molecular size of purified ViPs of approximately 250 kDa is obtained;

c. treating the purified ViPs of step (a) or step (b) with a cross linking agent EDAC;

d. activating the ViPs of step (c) with a linker molecule ADH in presence of EDAC;

e. treating the activated ViPs linked to a linker molecule ADH of step (d) at a concentration of 1 mg/ml to 5 mg/ml of purified ViPs of ~900 kDa or at a concentration of 5 mg/ml to 7.5 mg/ml of purified ViPs of ~250 kDa with a carrier protein in presence of EDAC to form the Vi-polysaccharide-carrier protein conjugate;

f. diafiltering through continuous buffer exchange with phosphate buffered saline of the Vi-polysaccharide-carrier protein conjugate of step (f) with a 1000 kDa membrane to obtain the purified ViPs-carrier protein vaccine antigen.

2.4. Conjugation of Vi-Polysaccharide and Tetanus Toxoid without a Linker:

The purified Vi polysaccharide (either size reduced or non-size reduced) were taken in the buffer of MES (2-morpholino ethane sulphonic acid), or PBS, or in physiological saline, at a pH varying from 5.0 to 9.0 (exact pH 6-7.5), the concentration of polysaccharide varies from 1.0 mg to 20 mg/ml (5 mg/ml). The protein were taken in the buffer like, MES, or PBS, or in physiological saline at a pH varying from 6.0 to 9.0 (exact pH 6-7.5), at a different concentration of 2.0 mg/ml to 20 mg/ml (10 mg/ml). Ratio of ViPs to protein should be between 1:1 to 1:3 meaning thereby if a total of 1 gm of ViPs is taken, then equivalent of 1 gm to 3 gm protein shall be subjected for conjugation. Conjugation was performed at 2° C.-8° C., to control the reaction rate effectively as compared to room temperature. At higher temperatures, the rate of conjugation is very fast. It is not preferable to expose polysaccharides to higher temperatures, since, after forming conjugates at higher temperatures, there lies possibilities of aggregation of the conjugated polysaccharides-protein molecules. This will increase the size of the molecules, which will become a difficulty to further purify the conjugate proteins in the subsequent steps. Hence, the conjugation is preferred at 2-8° C. The ViPs and TT were added together at a different concentration in any of the buffers described above at different pH conditions and incubated for conjugation. The time of incubation varies between 15-45 minutes at room temperature (25° C.), and within 1 hour to 2 hours at 2-8° C., whereas while following conjugation methodology using ADH (with linker), the incubation time required for conjugation is minimum 2-4 hrs at 2° C. to 8° C. Therefore, the total reaction time is also reduced following this method of conjugation without linker compared to conjugation with linker.

The final coupled molecules are concentrated and diafiltered using a 1000 kDa cut-off membrane preferably PES (polyether sulphone) membrane, followed by continuous buffer exchange using 20 diavolumes of phosphate buffered saline. The retentate which contained purified ViPs-TT is checked for polysaccharide-protein ratio which shall be within the ratio of 0.5% to 1.5%, Vi-content, protein content and molecular size distribution. Final conjugate bulk was sterile filtered using 0.22µ membrane and stored at 2-8° C.

Optionally, the final coupled molecules are concentrated and diafiltered using a 1000 kDa cut-off membrane preferably PES (polyether sulphone) membrane, using phosphate buffered saline and then loaded into a gel permeation column (Sepharose cross linked beads). Fractions collected which are within the ratio of 0.5% to 1.5% were pooled together, concentrated and checked for polysaccharide-protein ratio, Vi-content, protein content and molecular size distribution. Final conjugate bulk was sterile filtered using 0.22 g membrane and stored at 2-8° C.

The present conjugation methodology without any linker molecule was performed with an initial batch size of 10 gms of ViPs, which yielded 8 liters of ViPs conjugate bulk at a Vi conjugate concentration of 0.9 mg/ml 1.0 mg/ml which yielded 7-8 gms of ViPs-TT conjugate, thereby giving an yield of 70%-80%.

TABLE 2.2

Results of the ViPs-TT conjugate bulk without linker

| Tests | Results (in ranges) |
|---|---|
| Molecular size distribution | 74.3% of polysaccharide eluted at kDa 0.3 |
| Conjugate Vi content | 0.9 mg/ml-1.0 mg/ml |
| Free Vi Ps | 3%-6%. |
| Protein content | 0.75 mg/ml-0.8 mg/ml |
| Vi Ps/protein ratio | 1.2 |
| Free protein | Peak was not detectable at $17^{th}$-$18^{th}$ minute in HPLC UV (280 nm) chromatogram. Free protein is absent |
| Sterility | No growth was observed |

Figure 8:
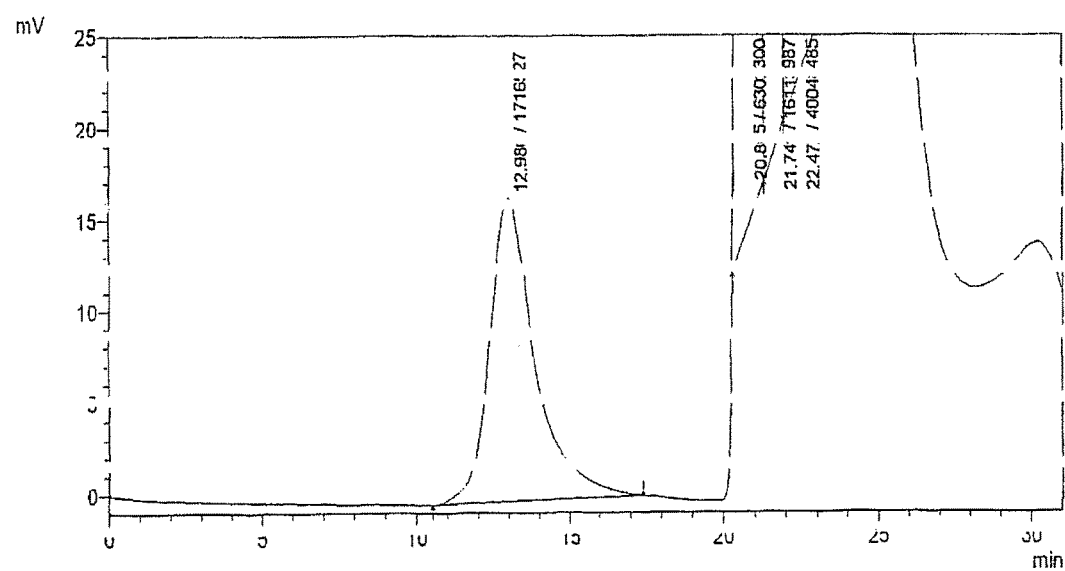
FIG. 8: HPLC (RI) for ViPs-TT conjugate bulk without linker. HPLC profile of the Vi-vi polysaccharide-Tetanus toxoid conjugate vaccine was detected by RI detector using HP-GPC column. The peak at 12.98 minutes represents conjugate ViPs-TT conjugate without linker.
Figure 9:
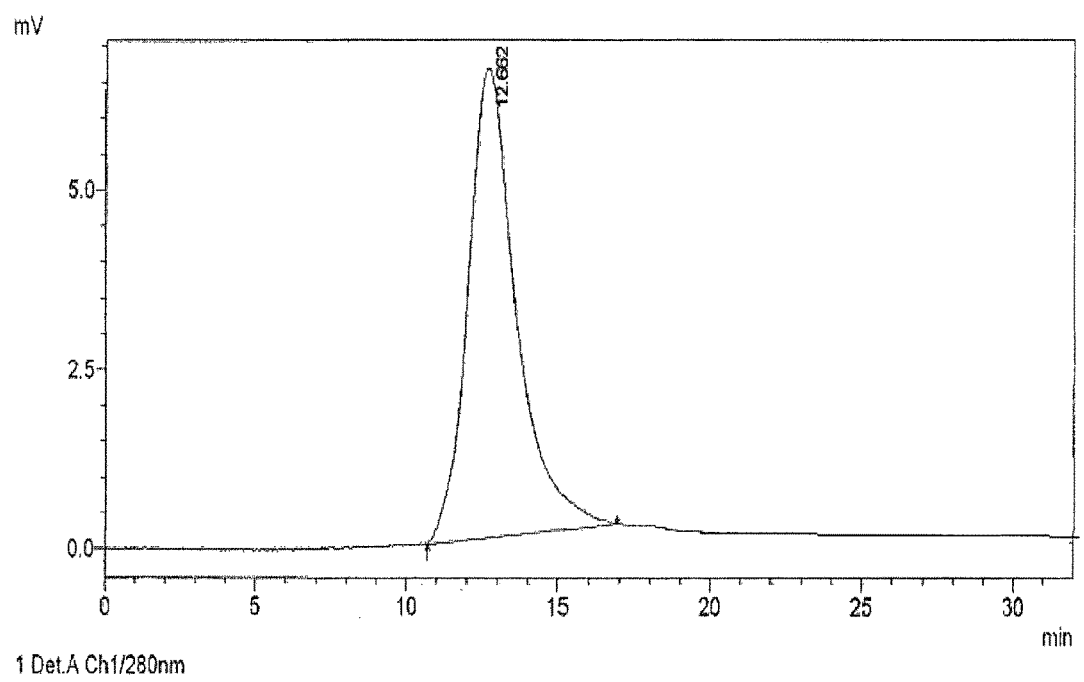
FIG. 9: HPLC (UV) for ViPs-TT conjugate bulk without linker. HPLC profile of the Vi-polysaccharide-Tetanus toxoid conjugate vaccine was detected by UV detector using HP-GPC column. The peak at 12.662 minutes represents conjugate ViPs-TT conjugate without linker.
Figure 10:
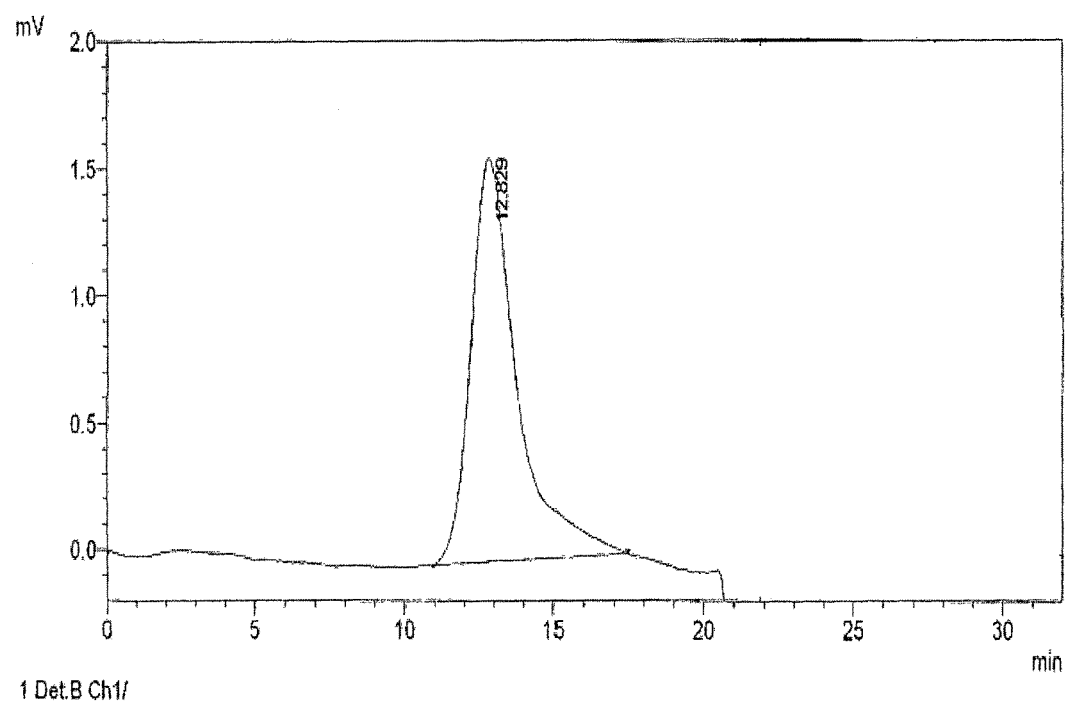
FIG. 10: HPLC (RI) for ViPs-TT conjugate vaccine. HPLC profile of the Vi-polysaccharide-Tetanus toxoid conjugate vaccine was detected by RI detector using HP-GPC column. The peak at 12.82 minutes represents conjugate ViPs-TT conjugate.
Figure 11:
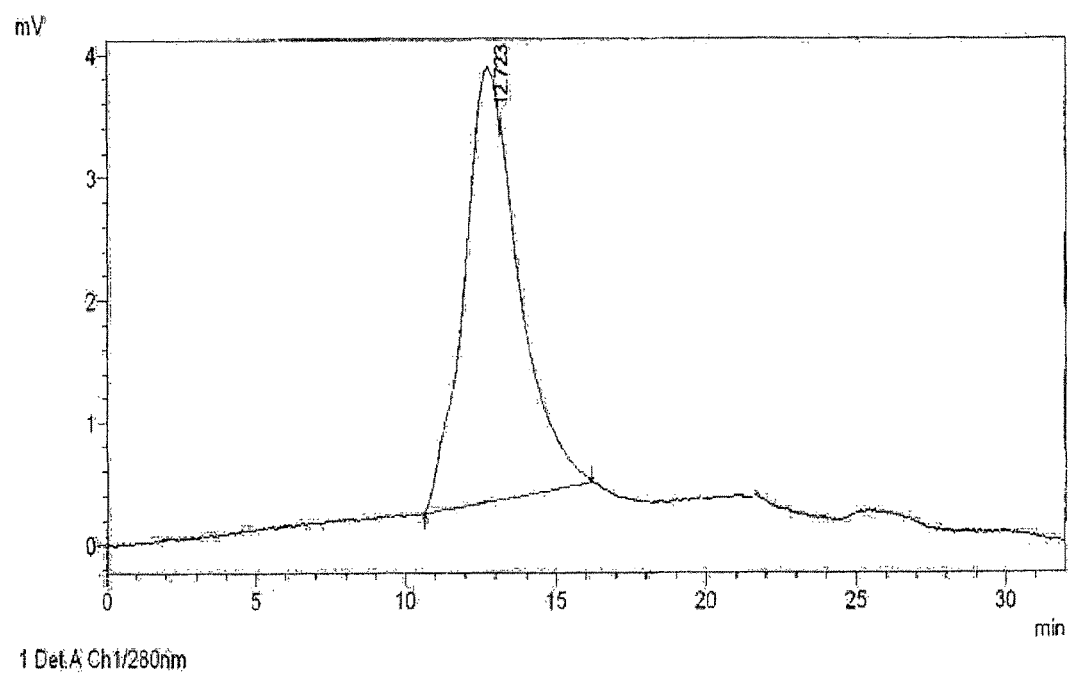
FIG. 11: HPLC (UV) for ViPs-TT conjugate vaccine. HPLC profile of the Vi-polysaccharide-Tetanus toxoid conjugate vaccine was detected by UV detector using HP-GPC column The peak at 12.72 minutes represents conjugate ViPs-TT conjugate.

The crude conjugate then obtained is purified by GPC, TFF, Ion Exchange or HIC. The conjugate matches all required specifications of pharmacopeia and further sterile filtered. FIGS. 8 to 9 represents HPLC Chromatograms of Vi-polysaccharide, and ViPs-TT Conjugate bulk at different stages without linker. All the given HPLC profiles clearly demonstrate the conjugation efficiency of the present methodologies.

The conjugation methodology without any linker molecule ADH to obtain a purified ViPs-TT conjugate vaccine antigen for preparation of a conjugate vaccine formulation against typhoid fever caused by *Salmonella typhi* as described above can be summarized with the following steps:

a. Fed-batch mode of cultivation to obtain purified ViPs with a feed medium, the feed medium comprising feeding a solution containing glucose at a range of 1 to 2 mg/mL concentration at a pH maintained in the range of 6.90 to 7.20 and dissolved oxygen level maintained between 40%-60%, wherein ammonia solution (50%) was supplied as a nitrogen source along with the feed medium;

b. optionally size reduction of ViPs, wherein the ViPs at a concentration of 5-7.5 mg/ml is subjected to high pressure homogenization at 1500 bar at 2-8° C. and the same activity repeated for at least 45 passes or by a microwave oven so that to a corresponding molecular size of purified ViPs of approximately 250 kDa is obtained;

c. treating the purified ViPs of step (a) or step (b) with a cross linking agent EDAC;

d. treating the carrier protein with the ViPs of step (c) at a concentration of 1 mg/ml to 5 mg/ml of purified ViPs of ~900 kDa or at a concentration of 5 mg/ml to 7.5 mg/ml of purified ViPs of ~250 kDa in presence of a cross linking agent EDAC to form the Vi-polysaccharide-carrier protein conjugate;

e. diafiltering through continuous buffer exchange with phosphate buffered saline of the ViPs-carrier protein conjugate of step (d) with a 1000 kDa membrane to obtain the purified ViPs-carrier protein vaccine antigen.

A linker molecule for example ADH, contains terminal amine groups at both the ends. The Vi native polysaccharide which is further reduced in its size prior to conjugation, contains abundant functional carboxyl groups (—COOH) naturally. Carrier proteins for example, tetanus toxoid contain both the amine (—$NH_2$) and the carboxyl groups (—COOH). In case of conjugation of the ViPs to the carrier protein with the help of a linker molecule ADH, is effected in presence of cross linking agents such as EDAC, wherein the —COOH group of the ViPs should bind with the one —$NH_2$ group of the ADH linker through one of its ends. The activated ViPs is coupled with the linker ADH, connected through a —CONH bond at one end of the ADH molecule. The other end of the ADH molecule remains free to be further bond with the —COOH group present in the carrier proteins at appropriate concentrations and temperature ranges. The activated ViPs-ADH is therefore again reacted with the carrier protein in presence of cross linking agent EDAC, which enables the —$NH_2$ present at the other end of the ADH molecule to bind with the —COOH group of the carrier protein molecule, thereby forming an effective bridge between the Vi-polysaccharide and the carrier protein. Thus in this method, there is a necessity remove excess linkers, after treating ViPs with ADH, and again after treating ViPs-ADH to carrier protein. Further EDAC is required to use twice in this method.

On the other hand, while following the methodology of conjugating ViPs with the carrier proteins without any linker molecule, since ViPs has free —COOH groups and the carrier proteins have free —$NH_2$ groups, it is possible to directly bond the —COOH of ViPs to the —$NH_2$ of the carrier proteins through treatment in presence of cross linking agents such as EDAC. The whole reaction is carried out within one step, which minimizes excessive use of EDAC as well as reduces the time to accomplish conjugation of ViPs to the carrier protein. Since all carrier proteins contain free —$NH_2$ groups, and ViPs also possesses free —COOH, it is possible to conjugate any carrier protein for example diphtheria toxoid, tetanus toxoid, CRM197 etc with Vi polysaccharide through this method. Thus, there lies no requirement of using any linker molecule (ADH) for conjugating the ViPs to the carrier protein. The advantage of conjugation without linker reflects in the stability of the conjugates, because of absence of any connecting molecular bridges between the ViPs and the carrier protein through ADH. This ensures better stability due to the improved strength of the ViPs-carrier protein conjugate (Vies-TT in this case) molecule in absence of any connecting bridges. Further degradation of the ViPs-TT is also reduced to very high extent. Also in this method, it is fairly easy to handle and carry out the experimentation. The total amount of EDAC required is lesser to about 50%, and handled only once instead of using twice in case of ADH linker method. (EDAC is an irritant potential of causing protein coagulation on prolonged exposure). Additionally, there is no requirement of GPC column or TFF system to remove excessive linkers. As the number of steps are reduced, we can minimize the loss of ViPs meant for conjugation to any carrier protein (for example TT), since the purification steps pertaining to ViPs-ADH linking are omitted. The following table exemplifies the completion of the entire conjugation experiment with reduced steps and the total time taken in comparison with and without linker molecule.

Total Time Taken in the Whole Conjugation Experiment:

TABLE 2.3

Comparison of time taken to complete the conjugation process.

| Experiment with ADH linker | | Experiment without ADH linker | |
|---|---|---|---|
| Activity | Time taken | Activity | Time Taken |
| Reaction of ViPs with ADH | 4 hrs | Not required | Not applicable |
| Removal of free ADH | 12-15 hrs | Not required | Not applicable |
| Analysis of % age ADH linked to ViPs | 2 hrs | Not required | Not applicable |
| Reaction of ViPs with TT | 2-4 hrs at 2° C. to 8° C. | Reaction of ViPs with TT | 1-2 hrs at 2° C. to 8° C. |
| Purification of ViPs-TT conjugate | 10 hrs | Purification of ViPs-TT conjugate | 10 hrs |
| ViPs-TT Fraction Analysis | 10 hrs | ViPs-TT Fraction Analysis | 10 hrs |
| Pooling and Sterile filtration | 3 hrs | Pooling and Sterile filtration | 3 hrs |
| Final conjugate analysis (HPLC, Vi-content, protein content, ratio) | 2 hrs | Final conjugate analysis (HPLC, Vi-content, protein content, ratio) | 2 hrs |
| Total time taken | 45-50 hrs | Total time taken | 25-27 hrs |

Example 3: Vaccine Formulation and Stability

A typical single dose of the typhoid conjugate vaccine formulation claimed under this invention comprises of Vi-TT conjugate as antigen from 15 microgram (μg) to 25 μg dissolved in normal saline made up to a total volume of 0.5 ml for one injection for a complete vaccination schedule.

The vaccine formulation as claimed under this invention is also made available in the form of multi-dose vials. Multi-dose vials may be either of 5 doses (for 5 different vaccinees/subjects/intended vaccine recipients), or 10 doses (for 10 different vaccinees/subjects/intended vaccine recipients). In case of multi-dose vials, preservatives are added to the vaccine formulation to avoid contamination of the vaccine formulation for multiple pricking of the vial in order to vaccinate 5-10 different children from the same vaccine multi-dose vial. The multi-dose vials of ViPs-TT typhoid conjugate vaccine formulation of the present invention uses a unique preservative 2-phenoxy ethanol, which is free from mercury chloride and thiomersal. Disadvantages of using conventional preservatives such as mercuric chloride and thiomersal contributing to carcinogenicity has been reported in the current state of the art. Therefore, use of this unique preservative 2-phenoxy ethanol overcomes the disadvantages of the conventional preservatives mercuric chloride and thiomersal. The details of the multidose vials and their formulation is tabulated below:

TABLE 3.1

Vaccine formulation of single dose and multidose vials

| Vaccine component | Single dose | 5 dose multi vial | 10 dose multi vial |
|---|---|---|---|
| Vi-TT conjugate | 15 μg to 25 μg | 75 μg to 125 μg | 150 μg to 250 μg |
| Preservative 2-phenoxy ethanol | Not required | 25 mg (10% v/v) | 50 mg (10% v/v) |
| Normal saline | Quantity sufficient | Quantity sufficient | Quantity sufficient |
| Dose Volume | 0.5 ml | 2.5 ml | 5.0 ml |

The stability of the ViPs-TT conjugate vaccine of BBIL has been studied and confirmed in detail for 3 years. The Vi Ps typhoid conjugate ViPs-TT vaccine was subjected for stability study of both accelerated storage conditions (25° C.±2° C.) for 6 months and real time storage conditions (2° C. to 8° C.) for 36 months and found that the test results obtained are within the limits and complies for the required specification (Table 3.2 to 3.5).

TABLE 3.2

Stability study of Typbar-TCV ™ (conjugated with linker molecule) at 2° C. to 8° C. (25 μg per dose Vi-TT of 0.5 ml)

| Time | Description A Clear, Colourless liquid, free from visible particles. by visual observation | Identification (Ouchterlony) Clear precipitation arc should be observed | pH 6.50 to 7.50 | O-acetyl content (Hestrin) 0.064 to 0.106 μmoles/dose | Vi content (Assay) 20-30 μg/dose | Free ViPs NMT 20% | Test for Pyrogens Summed responses of 3 rabbits should not exceed 1.15° C. | Abnormal Toxicity All Animals must Survive for seven days and show no weight Loss | Sterility Should comply with the Test for Sterility |
|---|---|---|---|---|---|---|---|---|---|
| Zero day | Complies | Complies | 7.08 | 0.099 | 29.30 | 6.3 | 0.6 | Complies | Complies |

TABLE 3.2-continued

Stability study of Typbar-TCV ™ (conjugated with linker molecule) at 2° C. to 8° C. (25 μg per dose Vi-TT of 0.5 ml)

| Time | Description A Clear, Colourless liquid, free from visible particles. by visual observation | Identification (Ouchterlony) Clear precipitation arc should be observed | pH 6.50 to 7.50 | O-acetyl content (Hestrin) 0.064 to 0.106 μmoles/ dose | Vi content (Assay) 20-30 μg/ dose | Free ViPs NMT 20% | Test for Pyrogens Summed responses of 3 rabbits should not exceed 1.15° C. | Abnormal Toxicity All Animals must Survive for seven days and show no weight Loss | Sterility Should comply with the Test for Sterility |
|---|---|---|---|---|---|---|---|---|---|
| 3rd month | Complies | Complies | 7.09 | 0.098 | 28.91 | 6.2 | 0.5 | Complies | Complies |
| 6th month | Complies | Complies | 7.15 | 0.093 | 28.45 | 5.9 | 0.6 | Complies | Complies |
| 9th month | Complies | Complies | 7.13 | 0.094 | 28.31 | 6.3 | 0.6 | Complies | Complies |
| 12th month | Complies | Complies | 7.03 | 0.091 | 27.89 | 6.3 | 0.6 | Complies | Complies |
| 18th month | Complies | Complies | 7.06 | 0.087 | 27.45 | 6.1 | 0.5 | Complies | Complies |
| 24th month | Complies | Complies | 7.15 | 0.089 | 27.16 | 5.7 | 0.6 | Complies | Complies |
| 36th month | Complies | Complies | 7.02 | 0.080 | 26.56 | 6.0 | 0.5 | Complies | Complies |

TABLE 3.3

Stability study of Typbar-TCV ™ (conjugated with linker molecule) at 25° C. ± 2° C. (25 μg per dose Vi-TT of 0.5 ml)

| Time | Description A Clear, Colourless liquid, free from visible particles. by visual observation | Identification (Ouchterlony) Clear precipitation arc should be observed | pH 6.50 to 7.50 | O-acetyl content (Hestrin) 0.064 to 0.106 μmoles/ dose | Vi content (Assay) 20-30 μg/ dose | Free ViPs NMT 20% | Test for Pyrogens Summed responses of 3 rabbits should not exceed 1.15° C. | Abnormal Toxicity All Animals must Survive for seven days and show no weight Loss | Sterility Should comply with the Test for Sterility |
|---|---|---|---|---|---|---|---|---|---|
| Zero day | Complies | Complies | 7.15 | 0.098 | 28.82 | 4.5 | 0.3 | Complies | Complies |
| 1st month | Complies | Complies | 7.13 | 0.097 | 28.52 | 4.1 | 0.4 | Complies | Complies |
| 2nd month | Complies | Complies | 7.16 | 0.095 | 27.94 | 4.4 | 0.5 | Complies | Complies |
| 3rd month | Complies | Complies | 7.12 | 0.093 | 27.35 | 4.9 | 0.5 | Complies | Complies |
| 6th month | Complies | Complies | 7.10 | 0.092 | 26.8 | 5.3 | 0.4 | Complies | Complies |

TABLE 3.4

Stability study of Typbar-TCV ™ (conjugated without linker molecule) at 2° C. to 8° C. (25 µg per dose Vi-TT of 0.5 ml)

| Time | Description A Clear, Colourless liquid, free from visible particles. by visual observation | Identification (Ouchterlony) Clear precipitation arc should be observed | pH 6.50 to 7.50 | O-acetyl content (Hestrin) 0.064 to 0.106 µmoles/dose | Vi content (Assay) 20-30 µg/dose | Free ViPs NMT 20% | Test for Pyrogens Summed responses of 3 rabbits should not exceed 1.15° C. | Abnormal Toxicity All Animals must Survive for seven days and show no weight Loss | Sterility Should comply with the Test for Sterility |
|---|---|---|---|---|---|---|---|---|---|
| Zero day | Complies | Complies | 7.03 | 0.101 | 29.60 | 6.0 | 0.5 | Complies | Complies |
| 3$^{rd}$ month | Complies | Complies | 7.05 | 0.095 | 27.93 | 6.3 | 0.7 | Complies | Complies |
| 6$^{th}$ month | Complies | Complies | 7.15 | 0.093 | 27.34 | 5.8 | 0.5 | Complies | Complies |
| 9$^{th}$ month | Complies | Complies | 7.10 | 0.094 | 27.63 | 6.0 | 0.5 | Complies | Complies |
| 12$^{th}$ month | Complies | Complies | 7.00 | 0.092 | 27.04 | 6.3 | 0.6 | Complies | Complies |
| 18$^{th}$ month | Complies | Complies | 7.02 | 0.086 | 25.28 | 6.2 | 0.6 | Complies | Complies |
| 24$^{th}$ month | Complies | Complies | 7.11 | 0.087 | 25.57 | 6.5 | 0.7 | Complies | Complies |
| 36$^{th}$ month | Complies | Complies | 7.04 | 0.086 | 25.28 | 6.7 | 0.5 | Complies | Complies |

TABLE 3.5

Stability study of Typbar-TCV ™ (conjugated without linker molecule) at 25° C. ± 2° C. (25 µg per dose Vi-TT of 0.5 ml)

| Time | Description A Clear, Colourless liquid, free from visible particles. by visual observation | Identification (Ouchterlony) Clear precipitation arc should be observed | pH 6.50 to 7.50 | O-acetyl content (Hestrin) 0.064 to 0.106 µmoles/dose | Vi content (Assay) 20-30 µg/dose | Free ViPs NMT 20% | Test for Pyrogens Summed responses of 3 rabbits should not exceed 1.15° C. | Abnormal Toxicity All Animals must Survive for seven days and show no weight Loss | Sterility Should comply with the Test for Sterility |
|---|---|---|---|---|---|---|---|---|---|
| Zero day | Complies | Complies | 7.10 | 0.093 | 27.30 | 5.0 | 0.3 | Complies | Complies |
| 1$^{st}$ month | Complies | Complies | 7.12 | 0.095 | 27.93 | 4.9 | 0.6 | Complies | Complies |
| 2$^{nd}$ month | Complies | Complies | 7.15 | 0.098 | 28.80 | 5.1 | 0.4 | Complies | Complies |
| 3$^{rd}$ month | Complies | Complies | 7.13 | 0.094 | 27.63 | 5.3 | 0.5 | Complies | Complies |
| 6$^{th}$ month | Complies | Complies | 7.11 | 0.095 | 27.93 | 5.7 | 0.6 | Complies | Complies |

Example 4: Clinical Trials

The final Vi-polysaccharide-tetanus toxoid conjugate bulks were formulated and tested for immunogenicity in Balb/c mice in comparison with native polysaccharide vaccine. Challenge study was carried to assess protective efficacy of the vaccine and preclinical trial was carried to ensure abnormal, acute and systemic toxicity in laboratory animals. Further, the effectiveness of the test vaccine Vi capsular polysaccharide-tetanus toxoid conjugate (Vi-TT) was studied at two different concentration doses (15 µg and 25 µg per dose) and revealed that both concentration elicited protective antibodies in infants, children's and adults. The immunogenicity and safety of BBIL's Vi-TT conjugate vaccine's typhoid Vi capsular polysaccharide-tetanus toxoid protein conjugate in comparison with reference vaccine (Salmonella typhi Vi-polysaccharide vaccine Typbar®) were evaluated.

In phase-II: A total 100 subjects were enrolled to evaluate the safety and immunogenicity of Typhoid Vi capsular polysaccharide-TT protein conjugate vaccine in comparison with reference Typhoid Vi capsular polysaccharide vaccine Typbar® in healthy teenagers of 13 to 17 years of age, children of 6-12 and 2-5 years old. The study demonstrated that the test vaccine Vi capsular polysaccharide-tetanus toxoid conjugate (Vi-TT) as superior to the reference Typhoid Vi capsular polysaccharide vaccine Typbar® with respect to the immunogenicity and reactogenicity in all age groups. The geometric mean of Vi IgG in terms of ELISA UNITS per milliliter (EU/ml) elevated more than four-fold raise 80%, 100% and 70% respectively when compared to the pre vaccinated sera for plain Typbar®.

The test Vaccine of Typhoid Vi Capsular Polysaccharide-tetanus toxoid conjugate Vaccine (Vi-TT) was administered 25 mcg/dose as single injection for age group 13-17 years teenagers and 2-6 years. The geometric mean of Vi IgG EU/ml elevated more than four-fold raise respectively 100% in both the age groups when compared to the pre vaccinated sera. Correspondingly the age group of 2-5 Years was injected with 25 μg/dose in two injections. The time interval for administration of second injection was 6 weeks respectively. The geometric mean of Vi IgG EU/ml elevated more than four-fold raise respectively 100% in this age group when compared to the pre vaccinated sera.

Another group was designed as 15 μg/dose as two injections for the age group between 2-5 Years age. The time interval for administration of second injection was 6 weeks respectively. The geometric mean of Vi IgG EU/ml elevated more than four-fold raise respectively 100% in the age group 2-5 years when compared to the pre vaccinated sera.

All test group injected with 25 μg as single injection, 25 μg as double injections per dose and 15 μg as double injection per dose showed 100% seroconversion. The antibody responses to the Vi-Polysaccharide-Tetanus Toxoid Protein conjugate vaccine is superior to the reference native polysaccharide vaccine in all age groups. Hence it can be concluded that the test vaccine Typhoid Vi Capsular Polysaccharide Tetanus Toxoid conjugate (Vi-TT) vaccine of BBIL was immunogenic to already commercially available reference vaccine Typbar® of BBIL.

Figure 12:
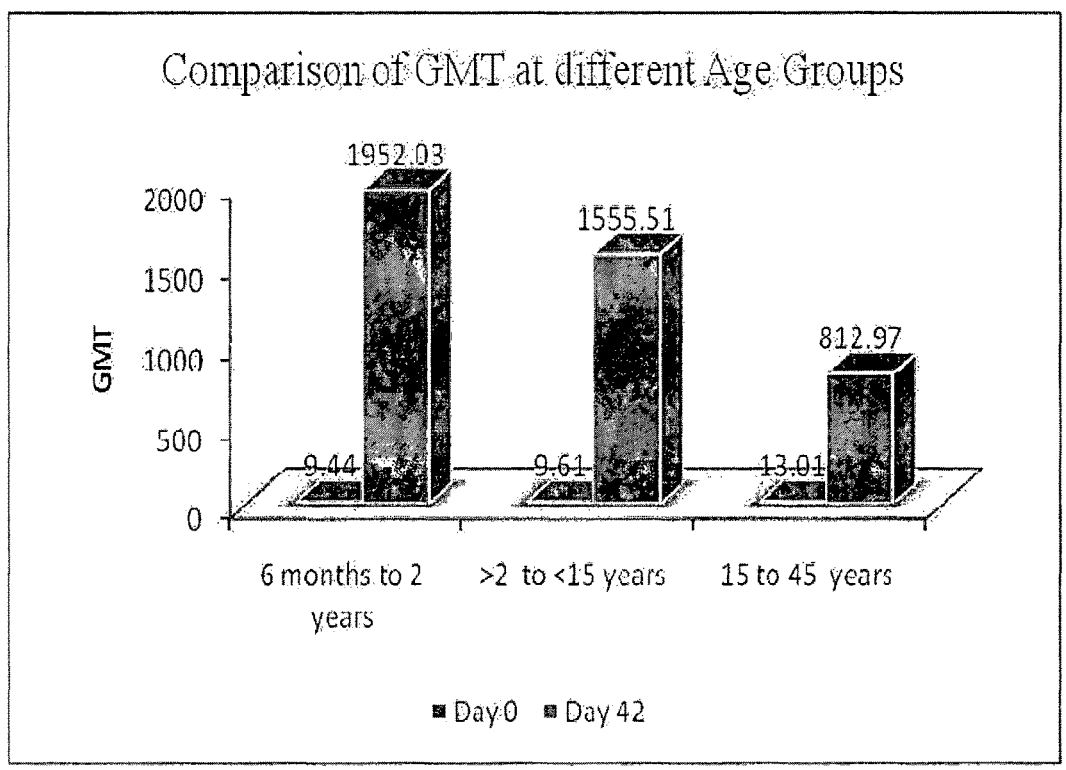
FIG. 12: Comparison of Geometric Mean Titer of different age groups after single injection of 25 μg single injection of ViPs-TT conjugate vaccine.

In Phase-III Details of number of subjects: A total of 981 subjects allocated to the Typhoid conjugate ViPs-TT vaccine and reference vaccine Typbar® to evaluate the immunogenicity and safety of Typhoid Vi-polysaccharide-TT conjugate vaccine ViPs-TT (Typbar-TCV™) Vs. plain Typhoid Vi-polysaccharide vaccine (Typbar®, Reference vaccine). BBIL's typhoid conjugate ViPs-TT vaccine, Geometric Mean Titre (GMT) and % seroconversion-4-fold was analysed between three-age groups (6 month to 2 year, >2 to <15 years and 15 to 45 years) for typhoid conjugate test ViPs-TT vaccine (Typbar-TCV™). The GMT in subjects in the age group between 6 months to 2 years, >2 to <15 years and 15 to 45 years in Typhoid-TT conjugate vaccine at day 42 were 1952.03 EU/ml, 1555.51 EU/ml, and 812.97 EU/ml of Typhoid anti Vi IgG antibody by ELISA respectively. The percentage of seroconversion (4-fold titre rise) in subjects in the age group between 6 months to 2 years, >2 to <15 years and 15 to 45 years in the in the Typhoid-TT conjugate vaccine was 98.05%, 99.17% & 92.13% respectively at day 42 (FIG. 12).

In 2 to <15 year age group GMT in Typhoid-TT conjugate Typbar-TCV™ vaccine and Typhoid vaccine Typbar® group on day 42 were 1555.51 EU/ml and 426.63 EU/ml of Typhoid anti Vi IgG antibody by ELISA respectively (p=0.00001). The percentage of seroconversion (4-fold titre rise) on day 42 between Typbar-TCV™ vaccine and Typhoid vaccine Typbar® 99.17% and 94.86% respectively (p=0.0086).

In 15 to 45 year age group GMT in Typbar-TCV™ vaccine and Typhoid vaccine Typbar® group on day 42 were 812.97 EU/ml and 376.81 EU/ml of Typhoid anti Vi IgG antibody by ELISA respectively (p=0.0001). The percentage of seroconversion (4-fold titre rise) on day 42 between Typbar-TCV™ vaccine and Typhoid vaccine Typbar® group 92.13% and 89.01% respectively (p=0.4737).

The superiority of Typhoid-TT (ViPs-TT) conjugate vaccine is 3.16 times higher than plain polysaccharide vaccine with respect to GMT post vaccination. The estimated GMT of Post to Pre titre ratio of typhoid conjugate vaccine (test) is 3.53 times higher than that of plain polysaccharide vaccine (reference). With respect to seroconversion typhoid conjugate vaccine is significantly superior to plain polysaccharide vaccine at a margin of 0.016%.

Figure 13:
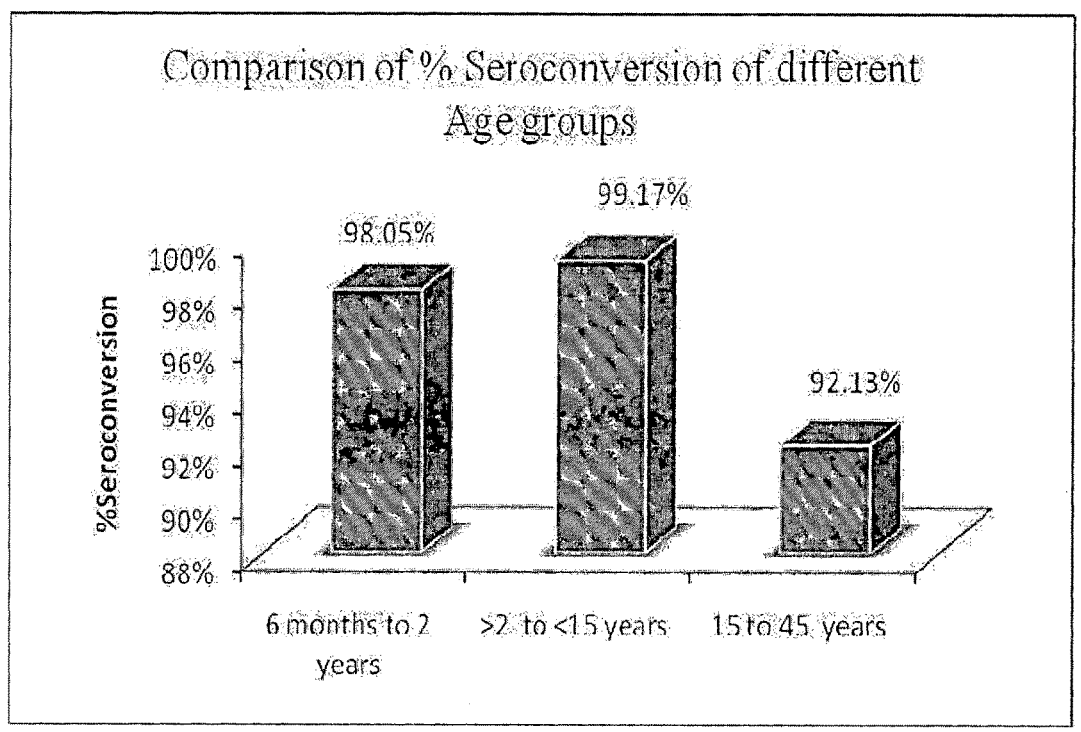
FIG. 13: Comparison of % age seroconversion of different age groups after single injection of 25 tag single injection of ViPs-TT conjugate vaccine.

Summary of phase III clinical trial data of ViPs-TT conjugate vaccine of BBIL Typbar-TCV™ is detailed below in comparison with reference vaccine Typbar® (FIGS. 12 and 13) and as well with Peda Typh™ is provided in the below tables:

TABLE 4.2

Typbar-TCV ™ vs. Typbar ®

| | Single injection of 25μg of ViPs-TT conjugate vaccine Typbar-TCV ™ of BBIL to comprise a complete vaccination schedule (single dose) | | Plain ViPs vaccine of BBIL Typbar ® | |
| --- | --- | --- | --- | --- |
| Age group | Geometric Mean Titre at day 42 (EU/ml) | % age Seroconversion on day 42 | Geometric Mean Titre at day 42 (EU/ml) | % age Seroconversion on day 42 |
| 6 months to 24 months | 1952.03 | 98.05% | Not applicable | Not Applicable |

TABLE 4.1

Typbar-TCV ™ phase III clinical trial data.

| | | Age group | | |
| --- | --- | --- | --- | --- |
| Response | Time period | 6 months to 2 years (N = 307) | 2 years to 15 years (N = 242) | 15 years to 45 years (N = 90) |
| GMT EU/ml (LCL, UCL) | Day 0 Day 42 | 9.44 (8.66, 10.31) 1952.03 (1795.48, 2122.23) | 9.61 (8.92, 10.35) 1555.51 (1371.33, 1764.43) | 13.01 (10.60, 15.97) 812.97 (637.66, 1036.46) |
| Seroconversion (% age) (4 fold) | Day 0 to Day 42 | 98.05% | 99.17% | 92.13% |

TABLE 4.2-continued

Typbar-TCV ™ vs. Typbar ®

| | Single injection of 25μg of ViPs-TT conjugate vaccine Typbar-TCV ™ of BBIL to comprise a complete vaccination schedule (single dose) | | Plain ViPs vaccine of BBIL Typbar ® | |
|---|---|---|---|---|
| Age group | Geometric Mean Titre at day 42 (EU/ml) | % age Seroconversion on day 42 | Geometric Mean Titre at day 42 (EU/ml) | % age Seroconversion on day 42 |
| 2 years to 15 years | 1555.51 | 99.17% | 426.03 | 94.86% |
| 15 years to 45 years | 812.97 | 92.13% | 376.81 | 89.01% |

Cytopathic Effect method (for Measles Vaccine) at 0 hrs, 4 hrs, 8 hrs and 12 hrs following incubation at 25° C. It was checked whether the physiochemical and biological parameters of both the vaccines were within specifications at the said temperature and time points. This study provided an overview of the laboratory findings for the reconstituted vaccine product for a short period of time.

TABLE 5.1

| Specification of Typhoid conjugate vaccine and measles vaccine | |
|---|---|
| Typhoid Conjugate Vaccine | Measles vaccine |
| Typbar-TCV ™ (ViPs-TT conjugate vaccine) Single dose-0.5 mL | Measles vaccine (LIVE) I.P (Freeze-dried) Single dose-0.5 mL |

Test Performed: 0-Acetyl Content by Hestrin's Method

Vi-polysaccharide is a linear homopolymer composed of (1-4)-2Oacetamido-2-deoxy-α-D-galacturonic acid that is O-acetylated at carbon-3. The O-acetyl content of the purified Vi-polysaccharide is important for the immunogenicity of Vi and it can be measured by using Hestrin's method.

TABLE 5.2

| | | O-acetyl content by Hestrin method | | |
|---|---|---|---|---|
| S. No. | Sample Detail | 0 Hour | $4^{TH}$ Hour | $8^{TH}$ Hour |
| 1. | Typbar-TCV ™ (ViPs-TT conjugate vaccine) at the start of time point 2-8° C. | 0.098 μmoles/dose | 0.098 μmoles/dose | 0.098 μmoles/dose |
| 2. | Typbar-TCV ™ (ViPs-TT conjugate vaccine) kept at 25° C. | 0.100 μmoles/dose | 0.100 μmoles/dose | 0.096 μmoles/dose |
| 3. | Measles Vaccine reconstituted with Typbar-TCV ™ (ViPs-TT conjugate vaccine) and kept at 25° C. | 0.151 μmoles/dose | 0.086 μmoles/dose | 0.058 μmoles/dose |
| | Specification | 0.064-0.106 μmoles/dose | 0.064-0.106 μmoles/dose | 0.064-0.106 μmoles/dose |

Example 5: TCV and Measles Interference Study

Typbar-TCV™ is a preparation of Vi-polysaccharide vaccine conjugated to Tetanus Toxoid carrier protein. It has been proven that children who received the Vi conjugate vaccine achieved and maintained higher levels of anti-Vi IgG serum antibodies compared to those who received the plain Vi-polysaccharide vaccine. Typbar-TCV™ (ViPs-TT conjugate vaccine) is proposed in the immunization schedule to have been administered between $6^{th}$ month to $24^{th}$ month, and preferably in the $9^{th}$ month from child birth. Since, Measles vaccine immunization is also done at the same time, to combine both the vaccines and administer as a single injection will provide added benefits. In order to be able to do this, the interference of the two vaccines on each other's biological and chemical properties needs to be explored. In line with the above proposal, a study was designed to reconstitute the lyophilized Measles vaccine with the liquid Typbar-TCV™ (ViPs-TT conjugate vaccine) and conduct O-acetyl content test (for Typbar-TCV™) and Results:

The Measles vaccine reconstituted with Typbar-TCV™ (ViPs-TT conjugate vaccine) was incubated at 25° C. was analyzed for O-acetyl content by Hestrin's method. As controls, the Typbar-TCV™ (ViPs-TT conjugate vaccine) kept at 2-8° C. and Typbar-TCV™ (ViPs-TT conjugate vaccine) at the start of time point 25° C. were also analyzed simultaneously. As expected, the O-acetyl content of the control samples at 2-8° C. and 25° C. were close to the initial value. The O-acetyl content of the combination vaccine (Measles+TCV) was higher than the acceptance criteria at 0 hrs (0.151 μmoles/dose). It decreased with time at 4 hrs and 8 hrs (0.086 and 0.058 moles/dose) which were within acceptance criteria, but different when compared to the Typbar-TCV™ only values at 2-8° C. and 25° C.

Test Performed: Potency Test by Cytopathic Effect (CPE) Method

Measles Vaccine is a live attenuated vaccine. To titrate the measles vaccine logarithmic dilution was prepared, each logarithmic dilution inoculated in to vero cell line with 8 replicates and incubated for 7-8 days and checked for the presence or absence of Cytopathic Effect. Virus titre is calculated by Spearman Karber formula. Results are as below:

TABLE 5.3

Potency test by Cytopathic Method
Results (log10 CCID50/0.5 mL) of Measles Interference Study with TCV

| S. No. | Sample Detail | 0 Hour | 4 Hour | 8 Hour | 12 Hours |
|---|---|---|---|---|---|
| 1 | Measles Vaccine reconstituted with its diluent at the start of each time point | 3.50 | | 3.40 | 3.50 |
| 2 | Measles Vaccine reconstituted with its diluent and kept at 25° C. | 3.50 | 3.45 | 3.50 | 3.40 |
| 3 | Measles Vaccine reconstituted with Typbar-TCV ™ (ViPs-TT conjugate vaccine) and kept at 25° C. | 3.30 | 3.15 | 3.00 | 2.80 |
| | Specification | | NLT 3.00 | | |

Results:

From the results, it is observed that Measles vaccine when reconstituted with its diluent, found stable for 12 hours and when reconstituted with the Typbar-TCV™ (ViPs-TT conjugate vaccine) is stable for 4 hours and fell between 4 and 8 hours.

We claim:

1. A vaccine formulation for prevention against typhoid fever caused by Salmonella typhi, comprising a partially de-O-acetylated capsular Vi-polysaccharide (ViPs) of Salmonella typhi conjugated to a carrier protein of tetanus toxoid forming a conjugate vaccine antigen, wherein:
    ViPs are derivatized with an adipic acid dihydrazde (ADH) linker prior to conjugation forming activated ViPs such that conjugation occurs between the activated ViPs and the carrier protein that is not derivatized with ADH, and
    no free ADH is attached to the carrier protein;
    the vaccine formulation elicits a T-dependent immune response against S. typhi; and
    the vaccine antigen is present in the vaccine formulation at a concentration of 5 µg to 25 µg per dose.

2. The vaccine formulation according to claim 1, wherein the vaccine antigen is present in the vaccine formulation at a concentration of 15-25 µg per dose.

3. The vaccine formulation according to claim 1, wherein the vaccine antigen is prepared by a method comprising:
    (a) subjecting ViPs at a concentration of 5-7.5 mg/ml to a microwave oven and treating with sodium bicarbonate so that a partially de-O-acetylated purified ViPs with corresponding molecular size of approximately 250-300 kDa is obtained;
    (b) treating the purified ViPs of step (a) with a cross linking agent EDAC;
    (c) activating the ViPs of step (b) with a linker molecule ADH in presence of EDAC;
    (d) treating the activated ViPs linked to a linker molecule ADH of step (c) at a concentration of 5 mg/ml to 7.5 mg/ml of purified partially de-O-acetylated ViPs of ~250-300 kDa with a carrier protein tetanus toxoid in presence of EDAC to form the Vi-polysaccharide-carrier protein conjugate; and
    (e) diafiltering through continuous buffer exchange with phosphate buffered saline of Vi-polysaccharide-carrier protein conjugate of step (d) with a 1000 kDa membrane to obtain the purified partially de-O-acetylated ViPs-carrier protein vaccine antigen, wherein the molecular size distribution of the ViPs-carrier protein conjugate molecule ranges from 0.25 kDa to 0.35 kDa.

4. The vaccine formulation according to claim 1, wherein the vaccine antigen is prepared by a method comprising:
    (a) subjecting ViPs at a concentration of 5-7.5 mg/ml to microwave oven and treating with sodium bicarbonate so that a partially de-O-acetylated purified ViPs with corresponding molecular size of approximately 250-300 kDa is obtained;
    (b) treating the purified ViPs of step (a) with a cross linking agent EDAC;
    (c) treating carrier protein tetanus toxoid with the ViPs of step (b) at a concentration of 5 mg/ml to 7.5 mg/ml conc. of partially de-O-acetylated purified ViPs of ~250-300 kDa in presence of a cross linking agent EDAC to form the Vi-polysaccharide-carrier protein conjugate; and
    (d) diafiltering through continuous buffer exchange with phosphate buffered saline of the ViPs-carrier protein conjugate of step (c) with a 1000 kDa membrane to obtain the purified partially de-O-acetylated ViPs-carrier protein vaccine antigen, wherein the molecular size distribution of the ViPs-carrier protein conjugate molecule ranges from 0.25 kDa to 0.35 kDa.

5. The vaccine formulation according to claim 3, wherein the yield of conjugate ViPs-carrier protein molecule ranges from 70% to 80%.

6. The vaccine formulation of claim 1, wherein the vaccine formulation is stable for 3 years at 2°-8° C., and for at least 6 months at 25° C.

7. The vaccine formulation of claim 1, wherein the percent seroconversion of the vaccine formulation is between 98% to 100% in case of age group 6 months to 24 months, 99% to 100% in the case of age group 2 years to 15 years, 90% to 100% in case of age group 15 years to 45 years, approximately 92.13% thereby providing four-fold increase seroconversion on $42^{nd}$ day post vaccination.

8. The vaccine formulation of claim 1, which, when administered to a patient in association with a measles vaccine formulation, shows no antigenic interference between the Vi-polysachcharide-tetanus toxoid conjugate antigen and the measles vaccine formulation.

9. The vaccine formulation according to claim 4, wherein the yield of conjugate ViPs-carrier protein molecule ranges from 70% to 80%.

10. The vaccine formulation of claim 8, wherein the measles vaccine formulation comprises a live attenuated measles virus.

11. The vaccine formulation of claim 1, wherein the T-dependent immune response against S. typhi is elicited in children below 2 years of age.

* * * * *